(12) United States Patent
Schenk et al.

(10) Patent No.: US 8,211,629 B2
(45) Date of Patent: Jul. 3, 2012

(54) LOW PRESSURE SPERM CELL SEPARATION SYSTEM

(75) Inventors: John L. Schenk, Fort Collins, CO (US); George E. Seidel, LaPorte, CO (US); Tae Kwang Suh, Fort Collins, CO (US)

(73) Assignee: XY, LLC, Navasota, TX (US)

( * ) Notice: Subject to any disclaimer, the term of this patent is extended or adjusted under 35 U.S.C. 154(b) by 0 days.

(21) Appl. No.: 10/523,268

(22) PCT Filed: Aug. 1, 2003

(86) PCT No.: PCT/US03/24460
§ 371 (c)(1),
(2), (4) Date: Jul. 7, 2005

(87) PCT Pub. No.: WO2004/012837
PCT Pub. Date: Feb. 12, 2004

(65) Prior Publication Data
US 2006/0121440 A1  Jun. 8, 2006

Related U.S. Application Data

(60) Provisional application No. 60/400,971, filed on Aug. 1, 2002.

(51) Int. Cl.
*A01N 1/02* (2006.01)
*G01N 33/00* (2006.01)
*A61B 17/43* (2006.01)
*A61D 7/00* (2006.01)

(52) U.S. Cl. .............. 435/2; 422/73; 600/33; 600/35

(58) Field of Classification Search ........ 435/2; 600/33, 600/35; 422/73
See application file for complete search history.

(56) References Cited

U.S. PATENT DOCUMENTS

| | | |
|---|---|---|
| 32,350 A | 2/1887 | Bhattacharya |
| 3,005,756 A | 10/1961 | VanDemark et al. |
| 3,299,354 A | 1/1967 | Hogg |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,738,759 A | 6/1973 | Dittrich et al. |
| 3,756,459 A | 9/1973 | Bannister |
| 3,761,187 A | 9/1973 | Dittrich et al. |
| 3,761,941 A | 9/1973 | Robertson |
| 3,788,744 A | 1/1974 | Friedman et al. |
| 3,791,384 A | 2/1974 | Richter et al. |
| 3,791,517 A | 2/1974 | Friedman |
| 3,810,010 A | 5/1974 | Thom |
| 3,816,249 A | 6/1974 | Bhattacharya |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,906,929 A | 9/1975 | Augspurger |
| 3,909,744 A | 9/1975 | Wisner et al. |
| 3,944,917 A | 3/1976 | Hogg et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| 4,006,360 A | 2/1977 | Mueller |
| 4,007,087 A | 2/1977 | Ericsson |
| 4,009,260 A | 2/1977 | Ericsson |
| 4,014,611 A | 3/1977 | Simpson et al. |
| 4,056,324 A | 11/1977 | Gohde |
| 4,058,732 A | 11/1977 | Wieder |
| 4,067,965 A | 1/1978 | Bhattacharya |
| 4,070,617 A | 1/1978 | Kachel et al. |
| 4,083,957 A | 4/1978 | Lang |
| 4,085,205 A | 4/1978 | Hancock |
| 4,092,229 A | 5/1978 | Bhattacharya |
| 4,110,604 A | 8/1978 | Haynes et al. |
| 4,148,718 A | 4/1979 | Fulwyler |
| 4,155,831 A | 5/1979 | Bhattacharya |
| 4,162,282 A | 7/1979 | Fulwyler et al. |
| 4,175,662 A | 11/1979 | Zold |
| 4,178,936 A | 12/1979 | Newcomb |
| 4,179,218 A | 12/1979 | Erdmann et al. |
| 4,189,236 A | 2/1980 | Hogg et al. |
| 4,191,749 A | 3/1980 | Bryant |
| 4,200,802 A | 4/1980 | Salzman et al. |
| 4,225,229 A | 9/1980 | Gohde |

(Continued)

FOREIGN PATENT DOCUMENTS

BR  9704313  6/1999

(Continued)

OTHER PUBLICATIONS

Rath, D et al. J Anim Sci 77:3346-3352, 1999.*
Chinese Patent Application No. 03818558.X; Office Action dated Mar. 24, 2006.
New Zealand Application No. 538462; Office Action dated Apr. 24, 2006.
Seidel, G.E. Jr., et al., Methods of Ovum Recovery and Factors Affecting Fertilization of Superovulated Bovine Ova, Control of Reproduction in the Cow, Sneenan ed., 1978, pp. 268-280.
Hawk, H. W. et al., Effect of Unilateral Cornual Insemination upon Fertilization Rate in Superovulating and Single-Ovulating Cattle, Journal of Animal Sciences, 1986 vol. 63, pp. 551-560
Andersson, M. et al., Pregnancy Rates in Lactating Holstein-Greisian Cows after Artificial Insemination with Sexed Sperm. Reprod. Dom. Anim 41, 95-97, 2006.

(Continued)

*Primary Examiner* — Marcia S Noble
(74) *Attorney, Agent, or Firm* — Craig R. Miles; CR Miles, P.C.

(57) ABSTRACT

A sperm cell process system providing to generate sperm cell insemination samples having controlled sperm cell fertility characteristics of sperm cells.

13 Claims, 2 Drawing Sheets

U.S. PATENT DOCUMENTS

| | | |
|---|---|---|
| 4,225,405 A | 9/1980 | Lawson |
| 4,230,558 A | 10/1980 | Fulwyler |
| 4,251,733 A | 2/1981 | Hirleman, Jr. |
| 4,255,021 A | 3/1981 | Brunsden |
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair |
| 4,367,043 A | 1/1983 | Sweet et al. |
| 4,395,397 A | 7/1983 | Shapiro |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Taboada et al. |
| 4,538,733 A | 9/1985 | Hoffman |
| 4,545,677 A | 10/1985 | Chupp |
| 4,559,309 A | 12/1985 | Evenson |
| 4,573,796 A | 3/1986 | Martin |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| 4,654,025 A | 3/1987 | Cassou et al. |
| 4,659,185 A | 4/1987 | Aughton |
| 4,660,971 A | 4/1987 | Sage et al. |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaucher |
| 4,680,258 A | 7/1987 | Hammerling et al. |
| 4,683,195 A | 7/1987 | Mullis et al. |
| 4,683,202 A | 7/1987 | Mullis |
| 4,683,213 A * | 7/1987 | Ax ................................ 436/501 |
| 4,691,829 A | 9/1987 | Auer |
| 4,698,142 A | 10/1987 | Muroi et al. |
| 4,702,598 A | 10/1987 | Bohmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,768 A | 1/1989 | Bond |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |
| 4,957,363 A | 9/1990 | Takeda et al. |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junnila |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,989,977 A | 2/1991 | North, Jr. |
| 4,999,283 A | 3/1991 | Zavos et al. |
| 5,005,981 A | 4/1991 | Schulte et al. |
| 5,007,732 A | 4/1991 | Ohki et al. |
| 5,017,497 A | 5/1991 | Gerard de Grooth et al. |
| 5,021,244 A | 6/1991 | Spaulding |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson |
| 5,138,181 A | 8/1992 | Lefevre et al. |
| 5,142,140 A | 8/1992 | Yamazaki et al. |
| 5,142,462 A | 8/1992 | Kashima |
| 5,144,224 A | 9/1992 | Larsen |
| 5,150,313 A | 9/1992 | Van den Engh et al. |
| 5,158,889 A | 10/1992 | Hirako et al. |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,204,884 A | 4/1993 | Leary et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |
| 5,260,764 A | 11/1993 | Fukuda et al. |
| 5,274,240 A | 12/1993 | Mathies et al. |
| 5,275,787 A | 1/1994 | Yuguchi et al. |
| 5,298,967 A | 3/1994 | Wells |
| 5,315,122 A | 5/1994 | Pinsky et al. |
| 5,316,540 A | 5/1994 | McMannis et al. |

| | | |
|---|---|---|
| 5,317,162 A | 5/1994 | Pinsky et al. |
| 5,346,990 A | 9/1994 | Spaulding |
| 34,782 | 11/1994 | Dandliker et al. |
| 5,359,907 A | 11/1994 | Baker et al. |
| 5,366,888 A | 11/1994 | Fry et al. |
| 5,367,474 A | 11/1994 | Auer et al. |
| 5,370,842 A | 12/1994 | Miyazaki et al. |
| 5,371,585 A | 12/1994 | Morgan et al. |
| 5,395,588 A | 3/1995 | North, Jr. et al. |
| 5,400,179 A | 3/1995 | Ito |
| 5,412,466 A | 5/1995 | Ogino |
| 5,437,987 A | 8/1995 | Ten et al. |
| 5,439,362 A | 8/1995 | Spaulding |
| 5,444,527 A | 8/1995 | Kosaka |
| 5,447,841 A | 9/1995 | Gray et al. |
| 5,447,842 A | 9/1995 | Simons |
| 5,452,054 A | 9/1995 | Dewa et al. |
| 5,457,526 A | 10/1995 | Kosaka |
| 5,461,145 A | 10/1995 | Kudo et al. |
| 5,464,581 A | 11/1995 | van den Engh |
| 5,466,572 A | 11/1995 | Sasaki et al. |
| 5,467,189 A | 11/1995 | Kreikebaum et al. |
| 5,469,375 A | 11/1995 | Kosaka |
| 5,471,294 A | 11/1995 | Ogino |
| 5,471,299 A | 11/1995 | Kaye et al. |
| 5,475,487 A | 12/1995 | Mariella, Jr. et al. |
| 5,480,774 A | 1/1996 | Hew et al. |
| 5,480,775 A | 1/1996 | Ito et al. |
| 5,483,469 A | 1/1996 | Van den Engh et al. |
| 5,488,469 A | 1/1996 | Yamamoto et al. |
| 5,492,534 A | 2/1996 | Atheyde |
| 5,494,795 A | 2/1996 | Guerry et al. |
| 5,495,719 A | 3/1996 | Gray, Jr. |
| 5,496,272 A | 3/1996 | Chung et al. |
| 5,503,994 A | 4/1996 | Shear et al. |
| 5,514,537 A | 5/1996 | Chandler |
| 5,523,573 A | 6/1996 | Hanninen et al. |
| 5,532,155 A | 7/1996 | Ranoux |
| 5,547,849 A | 8/1996 | Baer et al. |
| 5,548,395 A | 8/1996 | Kosaka |
| 5,548,661 A | 8/1996 | Price et al. |
| 5,550,058 A | 8/1996 | Corio et al. |
| 5,556,764 A | 9/1996 | Sizto et al. |
| 5,558,998 A | 9/1996 | Hammond et al. |
| 5,559,032 A | 9/1996 | Pomeroy et al. |
| 5,578,449 A | 11/1996 | Frasch et al. |
| 5,579,159 A | 11/1996 | Ito |
| 5,584,982 A | 12/1996 | Dovichi et al. |
| 5,589,457 A | 12/1996 | Wiltbank |
| 5,590,815 A | 1/1997 | Krasnoff et al. |
| 5,596,401 A | 1/1997 | Kusuzawa |
| 5,601,234 A | 2/1997 | Larue |
| 5,601,235 A | 2/1997 | Booker et al. |
| 5,601,533 A | 2/1997 | Hancke et al. |
| 5,602,039 A | 2/1997 | Van den Engh |
| 5,602,349 A | 2/1997 | Van den Engh |
| 5,608,519 A | 3/1997 | Grouley et al. |
| 5,620,842 A | 4/1997 | Davis et al. |
| 5,622,820 A | 4/1997 | Rossi |
| 5,627,037 A | 5/1997 | Ward et al. |
| 5,633,503 A | 5/1997 | Kosaka |
| 5,641,457 A | 6/1997 | Vardanega |
| 5,643,796 A | 7/1997 | Van den Engh et al. |
| 5,650,847 A | 7/1997 | Maltsev et al. |
| 5,658,751 A | 8/1997 | Yue et al. |
| 5,660,997 A | 8/1997 | Spaulding |
| 5,663,048 A | 9/1997 | Winkfein et al. |
| 5,665,315 A | 9/1997 | Robert et al. |
| 5,672,880 A | 9/1997 | Kain |
| 5,674,743 A | 10/1997 | Ulmer |
| 5,675,401 A | 10/1997 | Wangler et al. |
| 5,682,038 A | 10/1997 | Hoffman |
| 5,684,575 A | 11/1997 | Steen |
| 5,687,727 A | 11/1997 | Kraus et al. |
| 5,690,815 A | 11/1997 | Krasnoff et al. |
| 5,690,895 A | 11/1997 | Matsumoto et al. |
| 5,691,133 A | 11/1997 | Critser et al. |
| 5,693,534 A | 12/1997 | Alak et al. |
| 5,696,157 A | 12/1997 | Wang et al. |
| 5,699,152 A | 12/1997 | Fedor et al. |
| 5,700,692 A | 12/1997 | Sweet |
| 5,701,012 A | 12/1997 | Ho |
| 5,707,808 A | 1/1998 | Roslaniec et al. |
| 5,708,868 A | 1/1998 | Ishikawa |
| 5,712,807 A | 1/1998 | Bangham |
| 5,719,666 A | 2/1998 | Fukuda et al. |
| 5,719,667 A | 2/1998 | Miers |
| 5,726,009 A | 3/1998 | Connors et al. |
| 5,726,364 A | 3/1998 | Van den Engh |
| 5,726,751 A | 3/1998 | Altendorf et al. |
| 5,730,941 A | 3/1998 | Lefevre et al. |
| 5,736,330 A | 4/1998 | Fulton |
| 5,739,902 A | 4/1998 | Gjelsnes et al. |
| 5,745,308 A | 4/1998 | Spangenberg |
| 5,747,349 A | 5/1998 | den Engh et al. |
| 5,759,767 A | 6/1998 | Lakowicz et al. |
| 5,770,363 A | 6/1998 | Brown |
| 5,777,732 A | 7/1998 | Hanninen et al. |
| 5,780,230 A | 7/1998 | Li et al. |
| 5,786,560 A | 7/1998 | Tatah et al. |
| 5,790,692 A | 8/1998 | Price et al. |
| 5,793,485 A | 8/1998 | Gourley |
| 5,796,112 A | 8/1998 | Ichie |
| 5,798,276 A | 8/1998 | Haugland et al. |
| 5,799,830 A | 9/1998 | Carroll et al. |
| 5,804,436 A | 9/1998 | Okun et al. |
| 5,815,262 A | 9/1998 | Schrof et al. |
| 5,819,948 A | 10/1998 | Van den Engh |
| 5,824,269 A | 10/1998 | Kosaka et al. |
| 5,916,144 A | 10/1998 | Schandl et al. |
| 5,831,723 A | 11/1998 | Kubota et al. |
| 5,835,262 A | 11/1998 | Iketaki et al. |
| 5,840,504 A | 11/1998 | Blecher |
| 5,844,685 A | 12/1998 | Gontin |
| 5,846,737 A | 12/1998 | Kang |
| 5,866,344 A | 2/1999 | Georgiou |
| 5,868,767 A | 2/1999 | Farley et al. |
| 5,872,627 A | 2/1999 | Miers |
| 5,873,254 A | 2/1999 | Arav |
| 5,874,266 A | 2/1999 | Palsson |
| 5,876,942 A | 3/1999 | Cheng et al. |
| 5,880,457 A | 3/1999 | Tomiyama et al. |
| 5,880,474 A | 3/1999 | Norton et al. |
| 5,883,378 A | 3/1999 | Irish et al. |
| 5,888,730 A | 3/1999 | Gray et al. |
| 5,891,734 A | 4/1999 | Gill et al. |
| 5,893,843 A | 4/1999 | Rodrigues Claro |
| 5,895,764 A | 4/1999 | Sklar et al. |
| 5,895,922 A | 4/1999 | Ho |
| 6,704,313 B1 | 4/1999 | De Resende et al. |
| 5,899,848 A | 5/1999 | Haubrich |
| 5,909,278 A | 6/1999 | Deka et al. |
| 5,912,257 A | 6/1999 | Prasad et al. |
| 5,916,449 A | 6/1999 | Ellwart et al. |
| 5,917,733 A | 6/1999 | Bangham |
| 5,919,350 A | 7/1999 | Contaxis, III et al. |
| 5,919,360 A | 7/1999 | Contaxis, III et al. |
| 5,919,621 A | 7/1999 | Brown |
| 5,934,885 A | 8/1999 | Farrell et al. |
| 5,962,238 A | 10/1999 | Sizto et al. |
| 5,972,710 A | 10/1999 | Weigl et al. |
| 5,973,842 A | 10/1999 | Spangenberg |
| 5,985,216 A | 11/1999 | Rens et al. |
| 5,985,538 A | 11/1999 | Stachecju |
| 5,990,479 A | 11/1999 | Weiss et al. |
| 5,991,028 A | 11/1999 | Cabib et al. |
| 5,998,140 A | 12/1999 | Dervan et al. |
| 5,998,212 A | 12/1999 | Corio et al. |
| 6,002,471 A | 12/1999 | Quake |
| 6,003,678 A | 12/1999 | Van den Engh |
| 6,042,025 A | 3/2000 | Crampton et al. |
| 6,042,249 A | 3/2000 | Spangenberg |
| 6,050,935 A | 4/2000 | Ranoux et al. |
| 6,071,689 A | 6/2000 | Seidel et al. |
| 6,079,836 A | 6/2000 | Burr et al. |
| 6,086,574 A | 7/2000 | Carroll et al. |
| 6,087,352 A | 7/2000 | Trout |
| 6,090,947 A | 7/2000 | Dervan et al. |

| | | |
|---|---|---|
| 6,097,485 A | 8/2000 | Lievan |
| 6,111,398 A | 8/2000 | Graham |
| 6,117,068 A | 9/2000 | Gourley et al. |
| 6,119,465 A | 9/2000 | Mullens et al. |
| 6,120,735 A | 9/2000 | Zborowski et al. |
| 6,128,133 A | 10/2000 | Bergmann |
| 6,130,034 A | 10/2000 | Aitken |
| 6,132,961 A | 10/2000 | Gray et al. |
| 6,133,044 A | 10/2000 | Van den Engh |
| 6,133,995 A | 10/2000 | Kubota |
| 6,139,800 A | 10/2000 | Chandler |
| 6,140,121 A | 10/2000 | Ellington et al. |
| 6,143,535 A | 11/2000 | Paisson |
| 6,143,901 A | 11/2000 | Dervan |
| 6,146,837 A | 11/2000 | van de Winkel |
| 6,149,867 A | 11/2000 | Seidel et al. |
| 6,153,373 A | 11/2000 | Benjamin et al. |
| 6,154,276 A | 11/2000 | Mariella, Jr. |
| 6,175,409 B1 | 1/2001 | Nielsen et al. |
| 6,177,277 B1 | 1/2001 | Soini |
| 6,193,647 B1 | 2/2001 | Beebe et al. |
| 6,201,628 B1 | 3/2001 | Basiji et al. |
| 6,207,392 B1 | 3/2001 | Weiss et al. |
| 6,208,411 B1 | 3/2001 | Vaez-Iravani |
| 6,211,477 B1 | 4/2001 | Cardott et al. |
| 6,214,560 B1 | 4/2001 | Yguerabide et al. |
| 6,221,654 B1 | 4/2001 | Quake et al. |
| 6,221,671 B1 | 4/2001 | Groner et al. |
| 6,238,920 B1 | 5/2001 | Nagai et al. |
| 6,247,323 B1 | 6/2001 | Maeda |
| 6,248,590 B1 | 6/2001 | Malachowski |
| 6,256,096 B1 | 7/2001 | Johnson |
| 6,263,745 B1 | 7/2001 | Buchanan et al. |
| 6,283,920 B1 | 9/2001 | Eberle et al. |
| 6,296,810 B1 | 10/2001 | Ulmer |
| 6,309,815 B1 | 10/2001 | Tash et al. |
| 6,316,234 B1 | 11/2001 | Bova |
| 6,317,511 B1 | 11/2001 | Horiuchi |
| 6,322,901 B1 | 11/2001 | Bawendi et al. |
| 6,323,632 B1 | 11/2001 | Husher et al. |
| 6,326,144 B1 | 12/2001 | Bawendi et al. |
| 6,328,071 B1 | 12/2001 | Austin |
| 6,329,158 B1 | 12/2001 | Hoffman et al. |
| 6,332,540 B1 | 12/2001 | Paul et al. |
| 6,357,307 B2 | 3/2002 | Buchanan et al. |
| 6,368,786 B1 | 4/2002 | Saint-Ramon et al. |
| 6,372,422 B1 | 4/2002 | Seidel et al. |
| 6,372,506 B1 | 4/2002 | Norton |
| 6,384,951 B1 | 5/2002 | Basiji et al. |
| 6,395,305 B1 | 5/2002 | Buhr et al. |
| 6,400,453 B1 | 6/2002 | Hansen |
| 6,411,835 B1 | 6/2002 | Modell et al. |
| 6,411,904 B1 | 6/2002 | Chandler |
| 6,416,190 B1 | 7/2002 | Grier et al. |
| 6,423,505 B1 | 7/2002 | Davis |
| 6,423,551 B1 | 7/2002 | Weiss et al. |
| 6,432,630 B1 | 8/2002 | Blankenstein |
| 6,432,638 B2 | 8/2002 | Dervan et al. |
| 6,452,372 B1 | 9/2002 | Husher et al. |
| 6,454,945 B1 | 9/2002 | Weigl et al. |
| 6,456,055 B2 | 9/2002 | Shinabe et al. |
| 6,463,314 B1 | 10/2002 | Haruna |
| 6,465,169 B2 | 10/2002 | Walderich et al. |
| 6,473,176 B2 | 10/2002 | Basiji et al. |
| 6,482,652 B2 | 11/2002 | Furlong et al. |
| 6,489,092 B1 | 12/2002 | Benjamin et al. |
| 6,495,333 B1 | 12/2002 | Willmann et al. |
| 6,495,366 B1 | 12/2002 | Briggs |
| 6,503,698 B1 | 1/2003 | Dobrinsky et al. |
| 6,511,853 B1 | 1/2003 | Kopf-Sill et al. |
| 6,514,722 B2 | 2/2003 | Paisson et al. |
| 6,524,860 B1 | 2/2003 | Seidel et al. |
| 6,528,802 B1 | 3/2003 | Koenig et al. |
| 6,534,308 B1 | 3/2003 | Palsson et al. |
| 6,537,829 B1 | 3/2003 | Zarling et al. |
| 6,540,895 B1 | 4/2003 | Spence et al. |
| 6,563,583 B2 | 5/2003 | Ortyn et al. |
| 6,576,291 B2 | 6/2003 | Bawendi et al. |
| 6,577,387 B2 | 6/2003 | Ross, III et al. |
| 6,580,504 B1 | 6/2003 | Ortyn et al. |
| 6,587,203 B1 | 7/2003 | Colon |
| 6,589,792 B1 | 7/2003 | Malachowski |
| 6,590,911 B1 | 7/2003 | Spinelli et al. |
| 6,596,143 B1 | 7/2003 | Wang et al. |
| 6,596,499 B2 | 7/2003 | Jalink |
| 6,604,435 B2 | 8/2003 | Buchanan et al. |
| 6,613,525 B2 | 9/2003 | Nelson et al. |
| 6,617,107 B1 | 9/2003 | Dean |
| 6,618,143 B2 | 9/2003 | Roche et al. |
| 6,618,679 B2 | 9/2003 | Loehrlein et al. |
| 6,641,708 B1 | 11/2003 | Becker et al. |
| 6,642,018 B1 | 11/2003 | Koller et al. |
| 6,658,357 B2 | 12/2003 | Chandler |
| 6,664,550 B2 | 12/2003 | Rader et al. |
| 6,667,830 B1 | 12/2003 | Iketaki et al. |
| 6,671,044 B2 | 12/2003 | Ortyn et al. |
| 6,673,095 B2 | 1/2004 | Nordquist |
| 6,674,525 B2 | 1/2004 | Bardell et al. |
| 6,698,627 B2 | 3/2004 | Garcia et al. |
| 6,700,130 B2 | 3/2004 | Fritz |
| 6,703,621 B2 | 3/2004 | Wolleschensky |
| 6,706,163 B2 | 3/2004 | Seul et al. |
| 6,707,555 B1 | 3/2004 | Kusuzawa et al. |
| 6,713,019 B2 | 3/2004 | Ozasa et al. |
| 6,729,369 B2 | 5/2004 | Neas et al. |
| 6,746,873 B1 | 6/2004 | Buchanan et al. |
| 6,752,298 B2 | 6/2004 | Garcia et al. |
| 6,753,161 B2 | 6/2004 | Koller et al. |
| 6,761,268 B2 | 7/2004 | Garcia |
| 6,761,286 B2 | 7/2004 | Py et al. |
| 6,761,288 B2 | 7/2004 | Garcia |
| 6,767,706 B2 | 7/2004 | Quake |
| 6,780,377 B2 | 8/2004 | Hall et al. |
| 6,782,768 B2 | 8/2004 | Buchanan et al. |
| 6,789,706 B2 | 9/2004 | Abergel et al. |
| 6,789,759 B2 | 9/2004 | Heldt |
| 6,792,387 B2 | 9/2004 | Neas et al. |
| 6,793,387 B2 | 9/2004 | Neas et al. |
| 6,813,017 B1 | 11/2004 | Hoffman et al. |
| 6,819,411 B1 | 11/2004 | Sharpe et al. |
| 6,849,394 B2 | 2/2005 | Rozeboom et al. |
| 6,849,423 B2 | 2/2005 | Mutz et al. |
| 6,861,265 B1 | 3/2005 | Van den Engh |
| 6,941,005 B2 | 9/2005 | Lary et al. |
| 7,015,310 B2 | 3/2006 | Remington et al. |
| 7,071,917 B2 | 7/2006 | Christensen et al. |
| 7,094,527 B2 | 8/2006 | Seidel et al. |
| 7,105,355 B2 | 9/2006 | Kurabayashi et al. |
| 7,195,920 B2 | 3/2007 | Seidel et al. |
| 7,208,265 B1 | 4/2007 | Schenk |
| 7,221,453 B2 | 5/2007 | Sharpe et al. |
| 2001/0006416 A1 | 7/2001 | Johnson |
| 2002/0047697 A1 | 4/2002 | Husher et al. |
| 2002/0058332 A1 | 5/2002 | Quake et al. |
| 2002/0064809 A1 | 5/2002 | Mutz et al. |
| 2002/0096123 A1 | 7/2002 | Whittier et al. |
| 2002/0113965 A1 | 8/2002 | Roche et al. |
| 2002/0115055 A1 | 8/2002 | Matta |
| 2002/0119558 A1 | 8/2002 | Seidel et al. |
| 2002/0131957 A1 | 9/2002 | Gavin |
| 2002/0141902 A1 | 10/2002 | Ozasa et al. |
| 2002/0171827 A1 | 11/2002 | Van den Engh |
| 2002/0182590 A1 | 12/2002 | Strange et al. |
| 2002/0186375 A1 | 12/2002 | Asbury et al. |
| 2002/0186874 A1 | 12/2002 | Price et al. |
| 2002/0198928 A1 | 12/2002 | Bukshpan et al. |
| 2003/0002027 A1 | 1/2003 | Fritz |
| 2003/0048433 A1 | 3/2003 | Desjonqueres |
| 2003/0059764 A1 | 3/2003 | Ravkin et al. |
| 2003/0059945 A1 | 3/2003 | Dzekunov et al. |
| 2003/0078703 A1 | 4/2003 | Potts |
| 2003/0096405 A1 | 5/2003 | Takayama et al. |
| 2003/0098421 A1 | 5/2003 | Ho |
| 2003/0113765 A1 | 6/2003 | Dempcy et al. |
| 2003/0119050 A1 | 6/2003 | Shai |
| 2003/0119206 A1 | 6/2003 | Shai |
| 2003/0129091 A1 | 7/2003 | Seidel et al. |
| 2003/0157475 A1 | 8/2003 | Schenk |

| | | | |
|---|---|---|---|
| 2003/0165812 A1 | 9/2003 | Takayama et al. | |
| 2003/0175917 A1 | 9/2003 | Cumming | |
| 2003/0175980 A1 | 9/2003 | Hayenga et al. | |
| 2003/0190681 A1 | 10/2003 | Shai | |
| 2003/0207461 A1 | 11/2003 | Bell et al. | |
| 2003/0209059 A1 | 11/2003 | Kawano | |
| 2004/0005582 A1 | 1/2004 | Shipwash | |
| 2004/0031071 A1 | 2/2004 | Morris et al. | |
| 2004/0034879 A1 | 2/2004 | Rothstein et al. | |
| 2004/0049801 A1 | 3/2004 | Seidel | |
| 2004/0053243 A1 | 3/2004 | Evans | |
| 2004/0055030 A1 | 3/2004 | Maxwell et al. | |
| 2004/0061070 A1 | 4/2004 | Hansen | |
| 2004/0061853 A1 | 4/2004 | Blasenheim | |
| 2004/0062685 A1 | 4/2004 | Norton et al. | |
| 2004/0072278 A1 | 4/2004 | Chou et al. | |
| 2004/0107150 A1 | 6/2004 | Neas et al. | |
| 2004/0132001 A1 | 7/2004 | Seidel et al. | |
| 2005/0003472 A1 | 1/2005 | Anzar et al. | |
| 2005/0011582 A1 | 1/2005 | Haug | |
| 2005/0053910 A1 | 3/2005 | McKenzie et al. | |
| 2005/0064383 A1 | 3/2005 | Bashkin et al. | |
| 2005/0112541 A1 | 5/2005 | Durack | |
| 2005/0214733 A1 | 9/2005 | Graham | |
| 2005/0244805 A1 | 11/2005 | Ludwig et al. | |
| 2005/0282245 A1 | 12/2005 | Ludwig et al. | |
| 2006/0118167 A1 | 6/2006 | Neas et al. | |
| 2006/0121440 A1 | 6/2006 | Schenk et al. | |
| 2006/0147894 A1 | 7/2006 | Sowter | |
| 2006/0203226 A1 | 9/2006 | Roche et al. | |
| 2006/0263829 A1 | 11/2006 | Evans et al. | |
| 2006/0281176 A1 | 12/2006 | Seidel et al. | |
| 2007/0026378 A1 | 2/2007 | Schenk | |
| 2007/0026379 A1 | 2/2007 | Seidel et al. | |
| 2007/0092860 A1 | 4/2007 | Schenk | |
| 2007/0099171 A1 | 5/2007 | Schenk | |
| 2007/0099260 A1 | 5/2007 | Seidel et al. | |
| 2007/0117086 A1 | 5/2007 | Evans et al. | |
| 2007/0123461 A1 | 5/2007 | Josephson | |
| 2007/0248976 A1 | 10/2007 | Harding | |

| | | |
|---|---|---|
| WO | WO 99/44037 A1 | 9/1999 |
| WO | WO 00/06193 | 2/2000 |
| WO | WO 0129538 | 4/2001 |
| WO | WO 01/37655 A1 | 5/2001 |
| WO | WO 01/40765 A2 | 6/2001 |
| WO | WO 01/40765 A3 | 6/2001 |
| WO | WO 01/51612 A1 | 7/2001 |
| WO | WO 01/85913 A2 | 11/2001 |
| WO | WO 01/85913 A3 | 11/2001 |
| WO | WO 01/90295 A1 | 11/2001 |
| WO | WO 01/95815 A1 | 12/2001 |
| WO | WO 02/19943 A1 | 3/2002 |
| WO | WO 02/28311 A1 | 4/2002 |
| WO | 0241906 A2 | 5/2002 |
| WO | WO 02/41906 A2 | 5/2002 |
| WO | WO 02/43486 A1 | 6/2002 |
| WO | WO 02/43574 A2 | 6/2002 |
| WO | 03020877 A2 | 3/2003 |
| WO | WO 2004/009237 A2 | 1/2004 |
| WO | WO2004/009237 A2 | 1/2004 |
| WO | WO 2004/009237 A3 | 1/2004 |
| WO | WO 2004/012837 A2 | 2/2004 |
| WO | WO 2004/012837 A3 | 2/2004 |
| WO | WO 2004/017041 A2 | 2/2004 |
| WO | WO 2004/017041 A3 | 2/2004 |
| WO | WO 2004/024227 A2 | 3/2004 |
| WO | WO 2004/059282 A2 | 7/2004 |
| WO | WO 2004/003697 A2 | 10/2004 |
| WO | WO 2004/067177 A1 | 10/2004 |
| WO | WO 2004/086283 A3 | 10/2004 |
| WO | WO 2004/087177 A1 | 10/2004 |
| WO | WO 2004/088283 A2 | 10/2004 |
| WO | WO 2004/104176 A2 | 12/2004 |
| WO | WO 2004/104178 A3 | 12/2004 |
| WO | WO 2005/094652 A2 | 10/2005 |
| WO | WO 2005/095590 A2 | 10/2005 |
| WO | WO 2005/095960 A1 | 10/2005 |
| WO | WO 2006012597 A2 | 2/2006 |
| WO | 2006060770 A2 | 8/2006 |
| WO | 2007016090 A2 | 2/2007 |

FOREIGN PATENT DOCUMENTS

| | | |
|---|---|---|
| CN | 03109426.0 | 12/2005 |
| EP | 0025296 A2 | 3/1981 |
| EP | 0140616 | 5/1985 |
| EP | 0160201 A2 | 6/1985 |
| EP | 0288029 B1 | 4/1988 |
| EP | 0276166 A2 | 7/1988 |
| EP | A-0 365794 | 5/1990 |
| EP | 0461618 | 12/1991 |
| EP | 0468100 A1 | 1/1992 |
| EP | 0570102 A1 | 3/1993 |
| EP | 0538786 A | 4/1993 |
| EP | 606847 A2 | 7/1994 |
| EP | A-0 476155 | 1/1998 |
| EP | 1250897 A1 | 10/2002 |
| EP | 1403633 A3 | 4/2004 |
| GB | 1471019 | 4/1977 |
| JP | 61139747 A | 6/1986 |
| JP | 61159135 A | 7/1986 |
| JP | 2024535 | 1/1990 |
| JP | 4126064 A | 4/1992 |
| JP | 4126065 A | 4/1992 |
| JP | 4126066 A | 4/1992 |
| JP | 4126079 A | 4/1992 |
| JP | 4126080 A | 4/1992 |
| JP | 4126081 A | 4/1992 |
| WO | WO 88/07198 | 9/1988 |
| WO | WO 90/13315 A1 | 11/1990 |
| WO | 91/05236 | 4/1991 |
| WO | WO 93/17322 A1 | 9/1993 |
| WO | WO 96/12171 | 4/1996 |
| WO | WO 96/31764 | 10/1996 |
| WO | WO 98/34094 | 8/1998 |
| WO | WO 98/48259 | 10/1998 |
| WO | WO 99/05504 | 2/1999 |
| WO | WO 99/33956 | 7/1999 |
| WO | WO 99/38883 | 8/1999 |
| WO | WO 99/42810 | 8/1999 |

OTHER PUBLICATIONS

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

Johnson, L.A., et al, 1996 Gender preselection in mammals. XX Beltsville Symposium in Agricultural Research Technolgy's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low numbers of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

U.S. Appl. No. 11/422,735, filed May 25, 2006 entitled Apparatus, Methods and Processes for Sorting Particles and for Providing Sex-Sorted Animal Sperm.

Suh, T.K, et al., Pressure during flow sorting of bull sperm affects post-thaw motility characteristics; Theriogenology vol. 59, No. 1, Jan. 2003 p. 516.

Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, Tom and Currin, John Milk Production Evaluation in First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan The Dairy Industry $in Asia B. Japan; www.agnet.org/library/article/eb384b.html.

Crichton,E.; Huffman,S.;McSweeney,K.;and Schenk, J. 347 Artificial Insemination of Lactating Holstein Cows with sexed sperm: Abstract CSORP Publishing—Reproduction, Fertility and Development www.publish.csiro.au/nid/44/paper/RDv18n2Ab347.htm.

Lopez, H.,Caraviello, D.Z., Satter, L.D. ,Fricke, P.M. and Wiltbank, M.C.; Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology www.foodsci.uoguelph.ca/dairyedu/biosyntheses.html.

Milk Production Released Jul. 18, 2006, by the National Agricultural Statistics Service (NASS), Agri. Stats. Board, US Dept of Agri.

DeVries, A. Economic Value of Pregnancy in Dairy Cattle Journal of Dairy Sci. 89:3876-3885/American Dairy Sci. Assoc. 2006.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel *Anguilla japonica*, National Research Institute of Aquaculture, Nansei, Mie.

Morisawa, M. The Process of the Initiation of Sperm Motility; Laboratory of Physiology, Ocean Research Institute, University of Tokyo.

McGrady, A.V., at al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa , School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, September/October 616-624.

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp.

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and β-D-Glucuron idase Activity as Indicators of Sea Bass Semen Quality; Biology of Reproduction 70,1679-1684 (2004) Published online before print Feb. 11, 2004.

Parallel European Patent Application No. 03767201.1; Supplemental Search Report dated Oct. 24, 2006.

O'Brien, J. K. et al., Development of sperm sexing and associated assisted reproductive technology for sex preselection of captive bottlenose dolphins (*Tursiops truncatus*), Reproduction, Fertility and Development 2008, 18, 319-329.

Sharpe, Johnathan, Advances in flow cytometry for sperm sexing, Unpublished paper, 2008.

Johnson, S.K., Possibilities with today's reproductive technologies. Available online at www.sciencedirect.com; Therio 64(2005) pp. 639-656.

Brogliatti, G. et al., Pregnancy Rates and First Born Calves by Artificial Insemination using Sexed Semen in Argentina: Therio. Jan. 2, 2002, vol. 57, No. 1 . p. 369.

Palma, G. et al., Sperm Physiology: The Ability to Produce Embryos In Vitro using Semen from Bulls with a Low Non-Return Rate. Therio. p. 308.

Gottlinger, Christopher et al., Cell-Cooling in Flow Cytometry by Peltier Elements. Cytometry 7:295-297 (1986).

Abstracts: American Dairy Science Assoc., American Society of Animal Science, Jun. 22-26, 2003 Phoenix AZ. J.Anim Sci. vol. 81 Suppl.1/J. Dairy Sci. vol. 86, Suppl. 1.

Garner, Duane L., et al, Effect of Semen Dilution on Bovine Sperm Viability as Determined by Dual-DNA Staining and Flow Cytometry. J. of Andrology, vol. 18, No. 3 May/Jun. 1997.

Lindsey, A. L., et al., Hysteroscopic or rectally guided, deep-uterine insemination of mares with spermatozoa stored 18 h at either 5 °C or 15 °C prior to flow-cytometric sorting, Animal Reproduction Science, vol. 85, Issues 1-2, Jan. 2005, pp. 125-130.

Schenk, J. L., et al., Pregnancy rates in heifers and cows with cryopreserved sexed sperm: Effects of sperm numbers per inseminate, sorting pressure, and sperm storage before sorting, Theriogenology (2008), doi:10.1016/j. theriogenolology. 2008:08:016.

Suh, T.K., et al., High pressure flow cytometric sorting damages sperm, Theriogenology 64 (2005) 1035-1048.

Upreti, G. C., et al., Studies on aromatic amino acid oxidase activity in ram spermatozoa: role of pyruvate as an antioxidant, Animal Reproduction Science 51 (1998) 275-287.

Schafer, D. J., et al., Comparison of progestin-based protocols to synchronize estrus and ovulation before fixed-time artificial insemination in postpartum beef cows, Journal of Animal Science Mar. 30, 2007, pp. 1-21.

Lamb, G. C., Synchronization of estrus and artificial insemination in replacement beef heifers using gonadotropin-releasing hormone, prostaglandin F2a and progesterone, Journal of Animal Science Nov. 1, 2006, vol. 84, pp. 3000-3009.

Saladarriaga, J. P., Ovarian, hormonal, and reproductive events associated with synchronization of ovulation and timed appointment breeding in Bos indicus-influenced cattle using intravaginal progesterone, gonadotropin-releasing hormone, and prostaglandin F2a, Journal of Animal Science Jan. 2007, vol. 85, pp. 151-162.

O'Brien, J. K. et al., Semen collection, characterization an preservation in a beluga (*Delphinapterus leucas*), 1st International workshop on Beluga whale research, husbandry and management in wild and captive environments Mar. 2007.

Parallel New Zealand application No. 538462; Letters Patent dated Oct. 9, 2008 with effect from Aug. 1, 2003.

Parallel Australian application No. 2003/265362, Examination Report dated Sep. 4, 2008.

Parallel Japanese application No. 2004-526449, Notice of Allowance with allowed claims dated Aug. 29, 2010, 14 pages.

Parallel Canadian application No. 2,532,376, Office Action dated, Jun. 29, 2010, 4 pages.

Parallel European Application No. 03767201.1, Office Action dated Sep. 29, 2010, 5 pages.

Azmal et al. Relative merits of homo and heterospermic bull semen in respect of preservation quality. Pakistan Journal of Biol. Sci., Nov. 2004, vol. 7, pp. 1908-1911.

Beatty. Fertility of mixed semen from different rabbits. Journal or Reprod. Fertil. Feb. 1960, vol. 1, pp. 52-60.

"Applying Semen Sexing Technology to the AI Industry", National Association of Animal Breeders, Sep. 2000, pp. 1-16.

Akhtar, S., et al. 1995. Prevalence of Five Stereotypes of Bluetongue Virus in a Rambouillet Sheep Flock in Pakistan, Veterinary Record 136, p. 495.

Amann, R.P. and Seidel, G.E. Jr., 1982. Prospects for Sexing Mammalian Sperm, Animal Reproduction Laboratory College of Veterinary Medicine and Biomedical Sciences, Colorado State University, pp. 1-288.

Amoah, E.A. and Gelaye, S. 1996. Biotechnological advances in goat reproduction. J. Anim. Sci. 75(2):578-585.

Anderson, V.K., et al., 1973, Intrauterine und tiefzervikale Insemination mit Gefriersperma bein Schat. Zuchthygiene. 8:113-118.

Baker, R.D., et al., H.W. 1968. Effect of volume of semen, number of sperm and drugs on transport of sperm in artifically inseminated gilts. J. Anim. Sci. 27:88-93.

Batellier, F, Vidament M, Ducharep G, Arnaud G, Yvon JM, Fauquant J, Magistrini M., Advances in cooled technologies. Anim Reprod Sci 2001; In press, 68(3-4):181-190.

Barnes; F.L. and Eyestone: W.H., "Early Cleavage and the Maternal Zygotic Transition in Bovine Embryos", Theriogenology, vol. 33, No. 1, Jan. 1990, pp. 141-149.

Becker, S.E. and Johnson, A.L. 1992. Effects of gonadotropin releasing hormone infused in a pulsatite or continuous fashion on serum gonadotropin concentrations and ovulation in the mare. J. Anim. Sci. 70:1208-1215.

Bedford, S.J. and Hinrichs, K. 1994. The effect of insemination volume on pregnancy rates of pony mares. Theriogenology 42:571-578.

Berger, G.S. 1987, Intratubal insemination, Fert. Steril. 48:328-330.

Beyhan, Z., et al., 1998. Sexual dimorphism in IVF bovine embryos produced by sperm sorted by high speed flow cytometry. Theriogenology. 49(1):359. abstr.

Beyhan, Z., et al., 1999. Sexual dimorphism in IVM-IVF bovine embryos produced from X and Y Chromosome-Bearing spermatozoa sorted by high speed flow cytometry. Theriogenology. 52:35-48.

Blanchard, T. and Dickson, V., "Stallion Management", The Veterinary Clinics of North America, Equine Practice, vol. 8, No. 1, pp. 207-218 (1992).

Bracher, V. and Allen, W.R., "Videoendoscopic Examination of the Mare's Uterus: Findings in Normal Fertile Mares", Equine Veterinary Journal, vol. 24 (1992), pp. 274-278.

Braselton, W.E. and McShan, W.H. 1970. Purification and properties of follicle stimulating and luteinizing hormones from horse pituitary glands. Arch. Biochem. Biophys. 139:45-48.

Brethour, J.R. and Jaeger, J.R., "The Single Calf Heifer System", Kansas Agric. Sta. Rep of Progress 570, 1989.

Bristol, S.P. 1982. Breeding behavior of a stallion at pasture with 20 mares in synchronized oestrus. J. Reprod. Fert. Suppl. 32:71.

Brookes, A. J. and Obyme, M., "Use of cow-heifers in beef production", J. of the Royal Agricultural Society of England 126:30. (1965).

Buchanan, B.R., et al, "Insemination of Mares with Low Numbers of Either Unsexed or Sexed Spermatozoa", Theriogenology, vol. 53, pp. 1333-1344, (2000).

Burwash, L.D., et al., 1974. Relationship of duration of estrus to pregnancy rate in normally cycling, non-lactating mares. J.A.V.M.A. 165:714-716.

Caslick, E.A., "The Vulva and the Vulvo-vaginal Orifice and its Relation to Genital Health of the Thoroughbred Mare", Cornell Veterinarian, vol. 27, 1937, pp. 178-187.

Catt, et al., "Assesment of Ram and Boar Spermatozoa During Cell-Sorting by Flow Cytometry", Reproduction Dom Animal, vol. 32, pp. 251-258 (1997).

Catt, et al., "Birth of a Male Lamb Derived from an In Vitro Matured Oocyte Fertilized by Intracytoplasmic Injection of a Single Presumptive Male Sperm", Veterinary Record 139, 1996, pp. 494-495.

Chandler, J.E., "Videomicroscopic Comparison of Bull Sperm and Leukocyte Chromosome Areas as Related to Gender", J Dairy Sci 73, pp. 2129-2135, (1990).

Chandler, J.E., et al, "Bovine Spermatozoal Head Size Variation and Evaluation of a Seperation Technique Based on this Size", Theriogeneology 52, p. 1021-1034 (1999).

Chin, W.W. and Boime, I. 1990. In: Glycoprotein Hormones, Serona Symp. Norwell, MA, pp. 19-20.

Chung, Y.G., et al., 1998, Artificial insemination of superovulated heifers with 600,000 sexed sperm. J Anim. Sci. Suppl. 1. 836:215. abstr.

Clement, F., et al., 1998. Which insemination fertilizes when several successive inseminations are performed before ovulation. 7th Int. Symp. Eq. Repro. 151. abstr.

Cran, D.G., et al. 1997. Production of Lambs by Low Dose Intrauterine Insemination With Flow Cytometrically Sorted and Unsorted Semen, Scottish Agricultural College, UK, Theriogenology, p. 267.

Cran, D.G., et al., 1993, Production of Bovine Calves Following Separation of X-Chromosome and Y-Chromosome Bearing Sperm and In Vitro Fertilisation. Vet. Rec. 132:40-41.

Cran, D.G., et al., 1995. Sex preselection in cattle: a field trial. Vet. Rec. 136:495-496.

Cui, K., "Size Differences between human X and Y Spermatozoa and prefertilization diagnosis", Molecular Human Reproduction, vol. 3, No. 1, pp. 61-67, (1997).

Cui, K., "X Larger than Y", Nature 366, p. 177-118, (1993).

Curran, S. 1998, In: Equine Diagnostic Ultrasonography. Fetal gender determination. Rantanen & McKinnon. 1st Ed. Williams and Wilkins. pp. 165-169.

Day, B.N., et al., 1998. Birth of piglets preselected for gender following in vitro fertilization of in vitro matured pig oocytes by X and Y bearing spermatozoa sorted by high speed flow cytometry. Theriogenology. 49(1):360. abstr.

Dean, P.N., et al., 1978, Hydrodynamic orientation of spermatozoa heads for flow cytometry. Biophys. J. 23:7-13.

Demick, D.S., et al., 1976. Effect of cooling, storage, glycerization and spermatozoal numbers on equine fertility. J. Anim. Sci. 43:633-637.

DenDaas, J.H.G., et al., 1998. The relationship between the number of spermatozoa inseminated and the reproductive efficiency of dairy bulls. J Dairy Sci. 81: 1714-1723.

Dinnyes, A., et al., "Timing of the First Cleavage Post-insemination Affects Cryosurvival of In Vitro-produced Bovine Blastocysts", Molec Reprod develop 53, 1999, pp. 318-324.

Donaldson, L. E., "Effect of Insemination Regimen on Embryo Prodottion in Superovulated Cows", The Veterinary Record, Jul. 13, 1985, pp. 35-37.

Donoghue, A.M., et al., 1996. Timing of ovulation after gonadotropin induction and its importance to successful intrauterine insemination in the tiger (Panthera tigris), J. Reprod. Fert. 107:53-58.

Douglas, R.H. 1979. Review of superovulation and embryo transfer in the equine. Theriogenology. 11:33-46.

Douglas, R.H et al., 1974. Induction of ovulation and multiple ovulation on seasonally-anovulatory mares with equine pituitary fractions. Theriogenology. 2(6): 133-142.

Duchamp, G., et al., 1987. Alternative solutions to hCG induction of ovulation in the mare. J. Reprod. Fert. Suppl. 35:221-228.

Evans, M.J. and Irvine, C.H.G. 1977. Induction of follicular development, maturation and ovulation by gonadotropin releasing hormone administration to acyclic mares, Bio. Reprod. 16:452-462.

Fitzgerald, B.P., et al., 1993. Effect of constant administration of a gonadotropin-releasing hormone agonist on reproductive activity in mares: Preliminary evidence on suppression of ovulation during the breeding season. Am. J. Vet. Res. 54:1746-1751.

Fluharty, F.L., et al., "Effects of Age at Weaning and Diet on Growth of Calves", Ohio Agri. Res. and Dev. Circular, 1996, 156: 29.

Foulkes, J.A., et al., 1977. Artificial insemination of cattle using varying numbers of spermatozoa. Vet Rec. 101:205.

Francon, M. and Yamamoto, T., "Un Noveau et tres simple dispositif interferentiel applicable as microsepe", Optica Acta 9, p. 395-408 (1962).

Fugger, E.F., "Clinical Experience with Flow Cytometric Separation of Human X- and Y-Chromosome Bearing Sperm", Theriogenology, vol. 52, pp. 1435-1440 (1999).

Fulwyler, M.J. 1965. Electronic separation of biological cells by volume. Science. 150:910.

Falwyler, M.J. 1977. Hydrodynamic otientation of cells. J Histochem. Cytochem. 25:781-783.

Garner, D.L., et al., 1983. Quantification of the X and Y chromosome-bearing spermatozoa of domestic animals by flow cytometry. Biol. Reprod. 28:312-321.

Ginther, O.J. 1971. Some factors which alter estrus cycle in mares. J. Anim. Sci. 33:1158. abstr.

Ginther, O.J. 1992. In: Reproductive Biology of the Mare. (2nd Ed.) Equiservices, Cross Plains, WI, pp. 1-642.

Gledhill, B.L. 1988. Gender preselection: historical, technical and ethical perspective. Semin Reprod. Endocrinol. 6:385-395.

Gourley, D.D. and Riese, R.L. 1990. Laparoscopic artificial insemination in sheep. Vet. Clin. N. Amer: Food Anim. Prac. 6(3):615-633.

Grondahl, C., et al, "In Vitro Production of Equine Embryos", Biology of Reproduction, Monograph Series I, pp. 299-307 (1995).

Guillou, F. and Combarnous, Y. 1983. Purification of equine gonadotropins and comparative study of their acid-dissociation and receptor-binding specificity. Biochem. Biophys. Acta. 755:229-236.

Gurnsey, M.P., and Johnson, L.A., "Recent improvements in efficiency of flow cytometric sorting of X and Y-chromosome bering sperm of domestic animals: a review", 1998, New Zealand Society of Animal Protection, three pages.

Harrison, L.A., et al., 1991. Comparison of hCG, buserelin and luprostiol for induction of ovulation in cycling mares. Eq. Vet. Sci. 3:163-166.

Hofferer, S., et al., 1993. Induction of ovulation and superovulation in mares using equine LH and FSH separated by hydrophobic interaction chromatography. J. Reprod. Fert. 98:597-602.

Holtan, D.W., et al., 1977. Estrus, ovulation and conception following synchronization with progesterone, prostaglandin F2 and human chorionic gonadotropin in pony mares. J. Anim. Sci. 44:431-437.

Householder, D.D., et al., 1981. Effect of extender, number of spermatozoa and hCG on equine fertility. J. Equine Vet. Sci. 1:9-13.

Howard, J.G., et al., 1991. Comparative semen cryopreservation in ferrets (Mustela putorious furo) and pregnancies after laparoscopic intrauterine insemination with frozed-thawed spermatozoa. J. Reprod. Fert. 92:109-118.

Howard, J.G., et al., 1997. Sensitivity to exogenous gonadotropins for ovulation and laparoscopic artificial insemination in the cheetah and clouded leopard. Biol. Reprod. 56:1059-1068.

Hunter, R.H.F. 1980. Transport and storage of spermatozoa in the female reproductive tract. Proc 4th Int. Congr. Anim. Repro. and A.I. 9:227-233.

Hyland, J.H., et al., 1988. Gonadotropin-releasing hormone (GnRH) delivered by continuous infusion induces fertile estrus in mares during seasonal acyclicity. Proc. Amer. Assoc. Eq. Prac. 181-190.

Irvine, C.H.G. and Alexander, S.L. 1993 In: Equine Reproduction. Edited by McKinnon and Voss. Lea and Febiger. Philadelphia, London. pp. 37.

Jafar, et al., "Sex Selection in Mammals: A Review", Theriogenology, vol. 46, pp. 191-200 (1996).

Jasko, D.J., et al., "Effect of volume and concentration of spermatozoa on embryo recovery in mares", Theriogenology. 37:1233-1239, 1992.

Jasko DJ, Moran DM, Farlin ME, Squires EL, Amann RP, Pickett BW. Pregnancy rates utilizing fresh, cooled, and frozen-thawed stallion semen. Proc. 38th Ann Convention AAEP 1992: 649-660.

Johnson, A.L., "Pulsatile release of gonadotropin releasing hormone advances ovulation in cycling mares", Biol. Reprod. 35:1123-1130, 1986.

Johnson, A.L., et al. "Use of gonadotropin-releasing hormone (GnRH) treatment to induce multiple ovulations in the anestrous mare" Eq. Vet. Sci. 8:130-134, 1988.

Johnson, L., "Sex Preselection in Swine: Flow Cytometric Sorting of X- and Y-Chromosome Bearing Sperm to Produce Offspring", Boar Semen Preservation IV, 2000, pp. 107-114.

Johnson, L..A., "Sex Preselection in Rabbits: Live Births from X and Y Sperm Separated by DNA and Cell Sorting" Biology of Reproduction, vol. 41, pp. 199-203 (1989).

Johnson, L..A., "Advances in Gender Preselection in Swine" Journal of Reproduction and Fertiltiy Supplement, vol. 52, pp. 255-266 (1997).

Johnson, L..A., "Sex Preselection to Swine: Altered Sex Ratios in Offspring Following Surgical Insemination of Flow Sorted X- and Y-Bearing Sperm", Reproduction in Domestic Animals, vol. 26, pp. 309-314 (1991).

Johnson: L.A. 1994, Isolation of X- and Y-bearing spermatozoa for sex preselection. In: Oxford Reviews of Reproductive Biology. Ed. HH Charlton. Oxford University Press. 303-326.

Johnson, L.A. 1995. Sex preselection by flow cytometric separation of X and Y chromosome bearing spermatozoa based on DNA difference: a review. Reprod. Fert. Dev. 7:893-903.

Johnson, L.A. 1997. Advances in gender preselection in swine. J Reprod. Fert. Suppl. 52:255-266.

Johnson, L.A., "Gender preselection in Mammals: An overview", Deutsch. Tierarztl. Wschr, vol. 103, pp. 288-291 (1996).

Johnson, L.A., "Flow cytometric determination of spermatozoa sex ration in semen purportedly enriched for X or Y bearing spermatozoa" Theriogenology. 29:265. abstr, 1988.

Johnson, L.A., "Gender preselection in domestic animals using flow cytometrically sorted sperm" J Anim. Sci. Suppl 1.70:8-18. 1992.

Johnson, L.A., "The safety of sperm selection by flow cytometry" Ham. Reprod. 9(5):758, 1994.

Johnson, L.A., et al. "Sex Preselection. High-speed flow cytometric sorting of X and Y sperm for maximum efficiency", Theriogenology, vol. 52, (1999), pp. 1323-1341.

Johnson, L.A., et al., "Enhanced flow cytometric sorting of mammalian X and Y sperm: high speed sorting and orienting nozzle for artificial insemination", Theriogenology. 49(1):361. abstr., 1988.

Johnson, L.A., et al., "Flow sorting of X and Y chromosome bearing spermatozoa into two populations", Gam. Res. 16:203-212, 1987.

Johnson, L.A., et al., "Improved flow sorting resolution of X- and Y-chromosome bearing viable sperm separation using dual staining and dead cell gating" Cytometry 17 (suppl 7) 83, 1994.

Johnson, L.A., et al. "Modification of a Laser-Based flow Cytometer for High-Resolution DNA Analysis of Mammalian Spermatozoa", Cytometry 7, pp. 268-273 (1986).

Johnson, L.A., "Flow sorting of X and Y chromosome-bearing sperm for DNA using an improved preparation method and staining with Hoechst" 33342. Gam. Res. 17:1-9, 1987.

Kachel, et al., "Uniform Lateral Orientation, Caused by Flow Forces, of Flat Particles in Flow-Through Systems", The Journal of Histochemistry and Cytochemistry, 1997, vol. 25, No. 7, pp. 774-780.

Kanayama, K., et al., 1992b. Pregnancy by means of tubal insemination and subsequent spontaneous pregnancy in rabbits. J. Int. Med. Res. 20:401-405.

Kilicarslan, M.R., et al., 1996. Effect of GrnRH and hCG on ovulation and pregnancy in mares. Vet. Rec. 139:119-120.

Lapin, D.R. and Ginther, O.J. 1977. Induction of ovulatio and multiple ovulations in seasonally anovulatory and ovulatory mares with an equine pituitary extract. J. Anim. Sci. 44:834-842.

Lawrenz, R. 1985. Preliminary results of non-surgical intrauterine insemination of sheep with thawed frozen semen. J S Afr. Vet. Assoc. 56(2):61-63.

Levinson, G., et al., 1995. DNA-based X-enriched sperm separation as an adjunct to preimplantation genetic testing for the preparation of X-linked disease. Mol. Human Reprod. 10:979-982.

Lindsey, A., et al., "Hysteroscopic Insemination of Mares with Nonfrozen Low-dose Unsexed or Sex-sorted Spermatozoa", currently unpublished, pp. 1-15, Equin Vet J 34(2):121-127, 2002.

Lindsey, AC, Bruemmer JE, Squires EL. Low dose insemination of mares. Animal Reproduction Science 2001; In press, 68 (3-4): 279-89.

Linge, F. 1972. Faltforsok med djupfrost sperma (field trials with frozen sperm). Farskotsel. 52:12-13.

Lonergan, P., et al., "Effect of Time Interval from Insemination to First Cleavage on the Development of Bovine Embryos In Vitro and In Vivo", Theriogenology, 1999, p. 326.

Long, C.R., et al., 1998. Theriogenology. 49(1):363. abstr.

Loy, R.G. and Hughes, J.P. 1965. The effects of human chorionic gonadotropin on ovulation, length of estrus, and fertility in the mare. Cornell Vet. 56:41-50.

Macmillan, K.L. and Day, A.M., "Prostaglandin F2a: A Fertility Drug In Dairy Cattle?", Animal Research Station, Private Bag, Hamilton, New Zeland, Theriogenology, vol. 18 No. 3, pp. 245-253 (1982).

Matsuda, Y. and Tobari, I. 1988. Chromosomal analysis in mouse eggs fertilized in vitro with sperm exposed to ultraviolet light (UV) and methyl and ethyl methanesulfonate (MMS and EMS). Mutat. Res. 198:131-144.

Maxwell, W and Johnson, L., "Chlortetracycline Analysis of Boar Spermatozoa after Incubation, Flow Cytom Sorting, Cooling, or Cryopreservation", Molecular Reproduction and Development 46, 1997, pp. 408-418.

Maxwell, W.M.C., et al., 1993. Fertility of Superovulated Ewes after Intrauterine or Oviductal Insemination with Low Numbers of Fresh or Frozen-Thawed Spermatozoa. Reprod. Fertil. Dev. 5:57-63.

Maxwell WMC, Long CR, Johnson LA,, Dorbrinsky JR, Welch GR. The relationship between membrane status and fertility of boat spermatozoa after flow cytometric sorting in the presence or absence of seminal plasma. Reprod Fertil Dev 1998; 10:433-440.

McCue, P.M. 1996. Superovulation. Vet. Clin. N. Amer. Eq. Prac. 12:1-11.

McCue, P.M., et al., 1997. Oviductal insemination in the mare. 7th Int Symp. Eq. Reprod. 133. abstr, p. 1.

McDonald, L.E. 1988. Hormones of the pituitary gland. In: Veterinary Pharmacology and Therapeutics. 6th ed. Edited by N.H. Booth and L.E. McDonald. Ames, Iowa State Univ. Press. pp. 590.

McKenna, T. et al., 1990. Nonreturn rates of dairy cattle following uterine body or cornual insemination. J. Dairy Sci. 73:1179-1783.

McKinnon, A.O. and Voss, J.L. 1993. In: *Equine Reproduction*. Lea and Febiger. Philadelphia, London, p. 1-3288.

McKinnon, A.O., et al., 1993. Predictable ovulation in mares treated with an implant of the GnRH analogue deslorelin. Eq. Vet. J. 25:321-323.

McKinnon, A.O., et al., 1996. Repeated use of a GnRH analogue deslorelin (Ovuplant) for hastening ovulation in the transitional mare. Eq. Vet. J. 29:153-155.

McNutt, et al., "Flow Cytometric Sorting of Sperm: Influence on Fertilization and Embryo/Fetal Development in the Rabbits", Molecular Reproduction and Development, vol. 43, pp. 261-267 (1996).

Meinert, C., et al., "Advancing the time of ovulation in the mare with a short-term inplant releasing the GnRH analogue deslorelin", Equine Veterinary Journal, 25, pp. 65-68 (1993).

Merton, J., et al., "Effect of Flow Cytometrically Sorted Frozed/Thawed Semen on Success Rate of In Vitro Bovine Embryo Production", Theriogenology 47, 1997, pp. 295.

Meyers, P.J., et al., 1997. Use of the GnRH analogue, deslorelin acetate, in a slow release implant to accelerate ovulation in oestrous mares. Vet. Rec. 140:249-252.

Michaels, Charles, "Beef A.I. Facilities that work", Proc. Fifth N.A.A.B Tech. Conf. A.I. Reprod. Columbia, MO. pp. 20-22, 1974.

Michel, T.H., et al., 1986. Efficacy of human chorionic gonadotrophin and gonadatrophin releasing hormone for hastening ovulatio in Thoroughbred mares. Eq. Vet. J. 6:438-442.

Miller, S.J. 1986. *Artificial Breeding Techniques in Sheep* In Morrow, D.A. (ed): Current Therapy in Theriogenology 2. Philadelphia, WB Saunders, pp. 1143.

Mirskaja, L.M. and Petrapavlovskii, V.V. 1937. The reproduction of normal duration of heat in the mare by the administration of Prolan. Probl. Zivotn. Anim. Breed. Abstr. 5:387.

Molinia, F.C., et al., 1998. Successful fertilization after superovulation and laparoscopic intrauterine insemination of the brushtail possum, *Trichosurus vulpecula*, and tammar wallaby, *Macropus eugenii*. J.Reprod. Fert. 112:9-17.

Moran DM, Jasko, DJ, Squires EL, Amann RP. Determinational of Tempature and cooling rate which induce cold shock in stallion spermatozoa. Theriogenology 1992; 38:999-1012.

Morcom, C.B. and Dukelow, W.R. 1980. A research technique for the oviductal isemination of pigs using laparoscopy. Lab. Anim. Sci. 1030-1031.

Morris, L.H., et al., "Hysteroscopic insemination of small numbers of spermatozoa at the uterotubal junction of preovulatory mares", Journal of Reproduction and Fertility, vol. 118, pp. 95-100 (2000).

Muller, W. and Gautier, F. 1975. Interactions of heteroaromatic compounds with nucleic acids. Euro. J Biochem. 54:358.

Munne, S. 1994. Flow cytometry separation of X and Y spermatozoa could be detrimental to human embryos. Hum. Reprod. 9(5):758.

Nowshari, et al., "Superovulation of Goats with Purified pFSH Supplemented with Defined Amounts of pLH", Theriogenology, vol. 43, pp. 797-802 (1995).

Pace, M.M. and Sullivan, J.J. 1975. Effect of timing of insemination, numbers of spermatozoa and extender components on pregancy rates in mares inseminatied with frozen stallion semen. J Reprod. Fert. Suppl. 23:115-121.

Parrish, J.J. "Capacitation of Bovine Sperm by Heparin", Department of Meat and Animal Science, Biology of Reproduction 38, pp. 1171-1180(1988).

Peippo, J., et al., "Sex diagnosis of equine preimplantation embryos using the polymerase chain reaction", Theriogenology, vol. 44 619-627 (1995).

Penfold, L.M. et al., "Comparative Motility of X and Y Chromosome-Bearing Bovine Sperm Separated on the Basis of DNA Content", Mol. Reprod. and Develop. 1998, vol. 50, pp. 323-327.

Perry, E.J. 1968. Historical Background In: *The Artificial Insemination of Farm Animals*. 4th ed. Edited by E.J. Perry, New Brunswick, Rutgers University Press, pp. 3-12.

Petersen, G.A., et al, "Cow and Calf Performance and Economic Considerations of Early Weaning of Fall-Born Beef Claves", J. Anim. Sci., 1987, 64:15, pp. 15-22.

Pickett, B.W, et al., 1976. Factors influencing the fertility of stallion spermatozoa in an A.I. program. Proc. 8th Internat. Congr. Anim. Reprod. A.I. Krakow, Poland, 4: 1049-1052.

Pickett, B.W. and Back, D.G. 1973. Procedures for preparation, collection, evaluation and insemination of stallion semen. C.S.U. Exp. Sta. Artira. Reprod. Lab. Gen. Series Bull. 935.

Pickett, B.W., and Shiner, K.A., "Recent developments in artificial insemination in horses", Livestock Production Science, 40, pp. 31-36 (1994).

Pickett, B.W., et al., 1974. The effect of extenders, spermatozoal numbers and rectal palpation on equine fertility. Proc. Fifth N.A.A.B. Tech. Conf. A.I. Reprod. Columbia, MO. pp. 20-22.

Pickett, B.W., et al., 1975b. Effect of seminal extenders on equine fertility.J. Anim. Sci. 40:1136-1143.

Pickett, B.W., et al., 1978. Influence of seminal additives and packaging systems on fertility of bovine spermatozoa. J. Anim. Sci. Suppl. II. 47:12.

Pinkel, D., et al, "Flow Cytometric Determination of the Proportions of X- and Y-Chromosome-Bearing Sperm in Samples of Purportedly Separated Bull Sperm", Journal of Animal Science, vol. 60, pp. 1303-1307 (1998).

Pinkel, D., et al., 1982b. High resolution DNA measurements of mammalian spermatozoa. Cytometry. 3:1-9.

Province CA, Squires EL, Pickett BW, Amann RP. Cooling rates, storage temperatures and fertility of extended equine spermatozoa. Theriogenlolgy 1985; 23:925-934.

Rath, D., et al., "Low Dose Insemination Technique in the Pig", Boar Semen Preservation IV, 2000, pp. 115-118.

Rath, D., et al., "Production of Piglets Preselected for Sex Following in Vitro Fertilization with X and Y Chromosome-Bearing Spermatozoa Sorted by Flow Cytometry", Theriogenology, 47, pp. 795-800 (1997).

Rathi, R. et al., "Evaluation of In Vitro Capacitation of Stallion Spermatoza", Biology of Reproduction 2001, vol. 65, pp. 462-470.

Reiling, B.A., et al., "Effect of Prenatal Androgenization on Preformance, Location, and Carcass and Sensory Traits on Heifers in Single Calf Heifer System", J. Anim. Sci., 1995, 73: 986, pp. 986-992.

Rens, W., et al., "A Novel Nozzle for More Efficient Sperm Orientation to Improve Sorting Efficiency of X and Y Chromosome-Bearing Sperm", Technical Notes, Cytometry 33, 1998, pp. 476-481.

Rens, W., et al., "Improved Flow Cytometric Sorting of X- and Y-Chromosome Bearing Sperm: Substantial Increase in Yield of Sexed Semen", Molecular Reproduction and Development, 1999, pp. 50-56.

Rieger, D., et al, "The Relationship Between the Time of First Cleavage of Fertilized Cattle Oocytes and Their Development to the Blastocyst Stage", Theriogenology, 1999, pp. 190.

Rigby SL, Lindsey AC, Brinsko SP, Blanchard TL, Love CC, Varner DD. Pregnancy rates on mares following hysteroscopic or rectally-guided utero-tubal insemination with low sperm numbers. Proc $3^{rd}$ International Symposium on Stallion Reproduction 2001; 49 (abstr.).

Ritar, A. and Ball, A. 1991. Fertility of young cashmere goats after laparoscopic insemination. J. Agr. Sci. 117:271-273.

Roberts, J.R. 1971. In: Veterinary Obstetrics and Genital Diseases. Ithaca, New York. pp. 740-749.

Roser, JF., et al., 1980. Reproductive efficiency in mares with anti-hCG antibodies. Proc 9th Int. Congr. Anim. Repro. and A.I. 4:627. abstr.

Roth, T.L., et al., 1997. Effects of equine chorionic gonadotropin, human chorionic gonadotropin, and laparoscopic artificial insemination on embryo, endocrine, and luteal characteristics in the domestic cat. Bio Reprod. 57:165-171.

Rowley, H-S., et al., 1990. Effect of insemination volume on embryo recovery in mares. J. Equine Vet. Sci. 10:298-300.

Salamon, S. 1976. Artificial insemination of Sheep. Chippendale, New South Whales. Publicity Press. p. 83-84.

Schenk, J.L., "Cryopreservation of flow-sorted bovine spermatozoa", Theriogenology, vol. 52, 1375-1391 (1999).

Schenk, J.L. and Seidel, Jr., G.E., "Imminent Commercialization of Sexed Bovine", Proceedings, The Range Beef Cow Symposium XVL, 1999, pp. 89-96.

Schmid R.L., et al, "Fertilization with Sexed Equine Spermatozoa Using Intracytoplasmic Sperm Injection and Oviductal Insemination", 7th International Symposium On Equine Reproduction, pp. 139 (Abstract) (1998).

Seidel, G. Jr., "Use of Sexed Bovine Sperm for In Vitro Fertilization and Superovulation", Animal Reproduction and Biotechnology Laboratory, Colorado State University, Proceedings of the 2000 CETA/ACTE Convention, Charlottetown, Prince Edward Island, Aug. 2000, pp. 22-24.

Seidel, G.E. Jr. et al., "Artificial Insemination of Heifers with Cooled, Unfrozen Sexed Semen", Theriogenology, vol. 49 pp. 365 (Abstract) (1998).

Seidel, G.E. Jr, et al., "Insemination of Heifers with Sexed Sperm", Theriogenology, vol. 52, pp. 1407-1421 (1999).

Seidel, G.E. Jr., "Uterine Horn Insemination of Heifers With Very Low Numbers of Nonfrozen and Sexed Spermatozoa", Atlantic Breeders Cooperative, Theriogenology 48: pp. 1255-1264, (1997).

Seidel, G.E. Jr., et al., 1998. Artificial insemination of heifers with cooled, unfrozen, sexed semen. 1998. Theriogenology. 49(1):365. abstr.

Seidel, G.E., "Status of Sexing Semen for Beef Cattle", Texas A&M University 45th Annual Beef Cattle Short Course and Trade Show Proceedings, Aug. 9-11, 1999; pp. III 24-III 27.

Senger, P.L., et al., 1988. Influence of cornual insemination on conception rates in dairy cattle. J Anim. Sci. 66:3010-3016.

Shelton, J.N. and Moore, N.W. 1967. The response of the ewe tot pregnant serum mare gonadotropin and to horse anterior pituitary extract. J. Reprod. Fert. 14:175-177.

Shilova, A.V., et al., 1976. The use of human chorionic gonadothrophin for ovulation date regulation in mares. VIIIth Int. Congr. on Anim. Repro. and A.I. 204-208.

Squires, E., "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, pp. 127-130 (1996).

Squires, E.L., et al., 1994. Effect of dose of GnRH analogue on ovulation in mares. Theriogenology. 41:757-769.

Squires, E.L., "Early Embryonic Loss" in Equine Diagnostic Ultrasonography, $1^{st}$ Ed. pp. 157-163 Eds Rantanen & McKinnon. Williams and Wilkins, Baltimore, Maryland (1998).

Sullivan, J.J., et al., 1973. Duration of estrus and ovulation time in nonlactating mares given human chorionic gonadotropin during three successive estrous periods. J.A.V.M.A. 162:895-898.

Sumner, A.T. and Robinson, J.A., "A Difference in Dry mass between the heads of X and Y-bearing human Spermatozoa", J Reprod Fert 48, p. 9-15 (1976).

Taljaard, T.L., et al., 1991. The effect of the laparoscopic insemination technique on the oestrus cycle of the ewe. J.S Afr. Vet. Assoc. 62(2):60-61.

Taylor, C.S., "Efficiency of Food Utilization in Traditional and Sex-Controlled Systems of Beef Production", AFRC Animal Breeding Research Organization, West Mains Road, Edinburgh EH9 3JQ, pp. 401-440.

Tervit, H.R., et al., "Successful Culture In Vitro of Sheep and Cattle Ova", Agricultural Research Council, Unit of Reproduction Physiology and Biochemistry, University of Cambridge, 1972, p. 493-497.

Van Munster E.B., et al, "Difference in Volume of X- and Y-chromosome Bearing Bovine Sperm Heads Matches Difference in DNA Content" Cytometry 35 p. 125-128 (1999).

Van Munster E.B., et al, "Measurement-based evaluation of optical pathlength distributions reconstructed from simulated differential interference contrast images", Journal of Microscopy 192, Pt. 2, p. 170-176 (1998).

Van Munster, E.B., "Geslachtsbepaling met interferometrie", Derde prijs NtvN-prijsvraag voor pas-gepromoveerden 65/4, p. 95-98 (1999).

Van Munster, E.B., et al, "Difference in Sperm Head Volume as a Theoretical Basis for Sorting X & Y-Bearing Spermatozoa: Potentials and Limitations", Theriogenology 52, pp. 1281-1293, (1999).

Van Munster, E.B., et al, "Reconstruction of optical pathlength distributions form images obtained by a wide field differential interference contrast microscope", Journal of Microscopy 188, Pt. 2, p. 149-157 (1997).

Vazquez, J. et al., "Nonsurgical Uterotubal Insemination in the Mare", Proceedings of the 44th Annual Convention of the American Association of Equine Practitioners, vol. 44, pp. 68-69 (1998).

Vazquez, J., et al., "A.I. in Swine; New Strategy for Deep Insemination with Low Numbers of Spermatozoa Using a Non-surgical Methodology", $14^{th}$ International Congress on Animal Reproduction, vol. 2, Stockhlom, Jul. 2000, p. 289.

Vazquez, J., et al., "Successful Low-Dose Insemination by a Fiberoptic Endoscope Technique in the Sow", Proceedings Annual conference of the International Embryo Transfer Society, Netherlands, Theriogenology, vol. 53, Jan. 2000, pp. 201.

Vidament, M., et al., 1997. Equine frozen semen freezeability and fertility field results. Theriogenology. 48:907.

Vogel, T., et al, "Organization and expression of bovine TSPY", Mammalian Genome, vol. 8, pp. 491-496 (1997).

Voss, J.L., et al., 1974. Effect of human chorionic gonadotropin on duration of estrous cycle and fertility of normally cycling, nonlactating mares. J.A.V.M.A. 165:704-706.

Voss, J.L., et al., 1982. Effect of number and frequency of inseminations on fertility in mares. J. Reprod. Fertil. Suppl. 32:53-57.

Welch G.R., et al., 1994. Fluidic and optical modifications to a FACS IV for flow sorting of X- and Y-chromosome bearing sperm based on DNA. Cytometry 17(suppl. 7): 74.

Welch, G., et al., "Flow Cytometric Sperm Sorting and PCR to Confirm Separation of X- and Y-Chromosome Bearing Bovine Sperm", Animal Biotechnology, 6, pp. 131-139 (1995).

Wilson, C.G., et al., 1990. Effects of repeated hCG injections on reproductive efficiency in mares. Eq. Vet. Sci. 4:301-308.

Wilson, M.S. 1993. Non-surgical intrauterine artificial insemination in bitches using frozen semen. J.Reprod. Fert Suppl. 47:307-311.

Windsor, D.P., et al., "Sex Predetermination by Separation of X and Y Chromosome-bearing Sperm: A Review", Reproduction of Fertilizatio and Development 5, pp. 155-171, (1993).

Woods, J. and Ginther, O.J. 1983. Recent studies related to the collection of multiple embryos in mares. Theriogenology. 19:101-108.

Woods, J., et al., 1990. Effects of time of insemination relative to ovulation on pregnancy rate and embryonic-loss rate in mares. Eq. Vet. J. 22(6):410-415.

XP-002103478, File Biosis, (1988), one page (same as:Hawk, H.W., et al., "Fertilization Rates in Superovulating Cows After Deposition of Semen on the Infundibulum Near the Uterotubal Junction or After Insemination with High Numbers of Sperm", XP-002103478, Theriogenology, vol. 29, No. 5, pp. 1131-1142 (1988).

Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.

Aldrich, S. L., et al., "Parturition and Periperturient Reproductive and Metabolic Hormone Concentration in Prenatally Androgenized Beef Heifers", J. Anim. Sci. 73:3712. (1995).
Amann, R. P. et al., "Issues Affecting Commercialization of Sexed Sperm" Therio. 52:1441. (1999).
Amann., R P. "Fertilizing Potential Vitro of Semen from Young Beef Bulls Containing a High or Low Percentage of Sperm with a Proximal Droplet" Theriogenology 54: 1499-1515, 2000.
Amann, Rupert P. "Cryopreservation of Sperm" 1999, Encyclopedia of Reproduction 1:733-783.
American Meat and Science Association in Cooperation with National Livestock and Meat Board, "Research Guidelines for Cookery and Sensory Evaluation and Instrumental Tenderness Measurements for Fresh Meat". (1995).
Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).
Asbury, Charles A. "Fluorescence Spectra of DNA Dyes Measured in a Flow Cylometer," University of Washington Feb. 19, 1996.
Bagley, C. P. "Nutritional Management of Replacement Beef Heifers: a Review" J. Anim. Science 71:3155-3163. (1993).
Bailey, C. M. et al., "Nulliparous Versus Primiparous Crossbred Females for Beef", J. Anim. Sci, 69:1403. (1991).
Bakker Schut, Tom C. "A New Principle of Cell Sorting by Using Selective Electroportation in a Modified Flow Cytometry," University of Twente, Mar. 10, 1990.
Bahrman, S. J., et al., "Freeze Preservation of Human Sperm" American Journal of Obstetrics and Gynecology vol. 103 (5) p. 654-664 Mar. 1, 1969.
Bellows, R. A., et al., "Cause and Effect Relationships Associated With Calving Difficulty and Calf Birth Weight", J. Anim. Sci. 33:407. (1971).
Berardinelli, J. G., et al., "Source of Progesterolle Prior to Puberty in Beef Heifers". J. Anim. Sci. 49:1276, (1979).
Bergfeld, E. G., et al., "Ovarian Follicular Development in Prepubertal Heifers is Influenced by Level of Dietary Energy Intake", Bio. of Repro. 51:1051. (1994).
Berry, B. W., et al., "Beef Carcass Maturity Indicators and Palatability Attributes", J. Anim. Sci. 38:507 (1974).
Beyhan, Z., et al., 1999 Sexual Dimorphism in IVM-IVF Bovine Embryos Produced from X and Y Chromosome-Bearing Spermatozoa Sorted by High Speed Flow Cytometry. Theriogenology. 52: 35-48.
BigosBigos. Martin "Nine Color Eleven Parameter Immunophenotyping Using Three Laser Flow Cytometry," Stanford University Dec. 22, 1998.
Bioxcell, Bovine Sperm Preservation, Advertisement Jun. 28, 2005.
Bond, J., et al., "Growth and Carcass Traits of Open Beef Heifers Versus Beef Heifers That Have Calved", Nutrition Reports International 34:621. 1986.
Boucque, C. V., et al., "Beef-Production With Maiden and Once-Calved Heifers", Livestock Prod. Sci. 7:121. 1980.
Bourdon, R. M. and J. S. Brinks. "Simulated Efficiency of Range Beef—Production III, Culling Strategies and Nontraditional Management-Systems", J. Amin. Sci. 65:963. 1987.
Braun, J. et al, "Effect of Different Protein Supplements on Motility and Plasma Membrane integrity of Frozen-Thawed Stallion Spermatozoa". Cryobiology (1995) 32:487-492.
Buchanan, B.R. "Pregnancy Rates in Mares Following a Single Insemination with a Low Number of Spermatozoa into the Tip of the Uterine Horn" Theriogenology p. 395.
Burns, P. D. and Spitzer, J.C., "Influence of Biostimulation on Reproduction in Postpartum Beef-Cows", J. Anim. Sci. 70:358. 1992.
Byerley, D. J., et al., "Pregnancy Rates of Beef Heifers Bred Either on Puberal or Third Estrus". J Anim. Sci. 65:645. 1987.
Cave-Penney, Tony, "Sexed Semen Offers Faster Genetic Gain". Farming News, Livestock Supplement, Feb. 1997, p. 28.
Celestron: Telescope Basics: www.celestron.com/tb-2ref/htm; 4 pages.
Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.
Choi, Y.H. "Developmental Cappacity of Equine Oocytes Matured and Cultured in Equine Trophoblast-Conditioned Media" Theriogenoogy 56: 320-339, 2001.
Cran, D. G., et al., "The Predetermination of Embryonic Sex Using Flow Cytometrically Separated X and Y Spermatozoa" Human Reproduction Update 1996, vol. 2 (4) p. 355-63.
Crowley, J. P. "The facts of Once-Bred Heifer Production" School of Agric., Univ. of Aberdeen, Scotland. 1973.
da Silva, Coutinho M.A.,"Effect of time of oocyte collection and site of insemination on oocyte transfer in mares" Animal Reproduction and Biotechnology Laboratiory, Colorado State Uniuversity, Fort Collins Journal of Animal Science 2002. 80:1275-1279.
DakoCytomation, "MoFlo® Sorters" http://www.dakocytomation.us/prod_productrelatedinformation?url=gprod_moflo_index.htm one page, printed Jun. 26, 2003.
Database up 1 BR9704313 (Alves, De Resende et al) May 4, 1999.
de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.
Denham, A. "In-vitro studies on Sandhill Range Forage as Related to Cattle Preference", M.S. Thesis. Colorado State University, 1965.
Denk, Winfried. "Two-Photon Molecular Excitation in Laser-Scanning Microscopy," Handbook of Biological Confocal Microscopy, 1995.
Deutscher, G. H. "Extending Interval From Seventeen to Nineteen Days in the Melengestrol Acetate-Prostaglandin Estrous Synchronization Program for Heifers". The Professional Animal Scientist 16:164. 2000.
Diagnostic Products Corporation. "Coat-A-Count" http://www.Progesterone.com. 1998.
Dikeman, M. E. "Cattle Production Systems to Meet Future Consumer Demands" J. Anim. Sci. 59:1631, 1984.
Dippert, K.D. "Fertilization Rates in Superovulated and Spontaneously Ovulating Mares" Theriogenology 41: 1411-1423, 1994.
Doyle, S. P., et al. "Artificial Insemination of Lactating Angus Cows with Sexed Semen". Proc. Western Sect. Am. Soc. Anim. Sci. 50:203. 1999.
Dresser D.W. et al. Analysis of DNA content of Living Spermatozoa Using Flow Cytometry Technique Journal of Reproduction and Fertility, 1993, vol. 98, pp. 357-365.
Ferrell, C. L. Effects of Post-Weaning Rate of Gain on Onset of Puberty and Productive Performance of Heifers of Different Breeds. J. Anim. Sci. 55:1272. 1982.
Ferrell, C. L. and T. G. Jenkins. "Energy-Utilization by Mature, Nonpregnant, Nonlactating Cows of Different Types" J. Anim. Sci. 58:234. 1984.
Field, R. A., et al., "Bone-Ossification and Carcass Characteristics of Wethers Given Silastic Implants Containing Estradiol", J. Anim. Sci. 68:3663-3668. 1990.
Field, R. et al., "Growth, Carcass, and Tenderness Characteristics of Virgin, Spayed, and Single-Calf Heifers", J. Anim. Sci. 74:2178. 1996.
Foote, et al. Motility and Fertility of Bull Sperm Frozen-Thawed Differently in Egg Yolk and Milk Extenders Containing Detergent, 1987 J Dairy Sci 70:2642-2647.
Foote, R.H., "Buffers and Extenders: What Do They Do? Why Are They Important?" Proc of the NAAB Tech. Conf. on Artificial Insemination and Reproduction, 62-70 (1984).
Fuller, Robert R. "Characterizing Submicron Vesicles With Wavelenth-Resolved Fluorescence in Flow Cytometry," University of Illinois, May 13, 1996.
Ginther, O. J., "Sexual Behavior Following Introduction of a Stallion into a Group of Mares" Therio. vol. 19 (6) Jun. 1983.
Gombe, S. and Hansel, W. "Plasma Luteinizing☐Hormone (LH) and Progesterone Levels in Heifers on Restricted Energy Intakes." J. Anim. Sci. 37:728. 1973.
Gottlinger et al., "Operation of a Flow Cytometer", Flow Cytometry and Cell Sorting, A. Radbruch (Ed.), 1992, pp. 7-23.

Graham, J. Analysis of Stallion semen and its Relation to Fertility. Abstract Complete article from Reproductive Technology vol. 12 # Apr. 1, 1996 now included in XYIDS000213.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production*. 59 (1975).

Gregory. K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Penorrance of Early and Normal☐Weaned Calves", I. Prod. Agric, 4:168 (1991).

Hall, J. B., et al., "Effect of Age and Pattern of Gain on Induction of Puberty with a Progestin in Beef Heifers." J. Anim. Sci. 75:1606 (1997).

Hamamatsu "*Technical Information, Optical Detector Selection: A Delicate Balacning Act*", web page, http://www.optics.org/hamamatsu/photodiode.html, printed on Apr. 15, 2000, 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive." Journal of Andrology, 11:1:73-88 (1990).

Harte, F. J. "System of Production of Beef From Once Calved Heifers." In: J.C. Taylor (Ed.) *The Early Calving of Heifers and its Impact on Beef Production*. 123 (1975).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hohenboken, W. D. "Applications of sexed semen in cattle production." Therio. 52:1421. 1999.

Horan, Paul K. "Quantitative Single Cell Ana,lysis and Sorting, Rapid Analysis and sorting of cells is emerging as an important new technology in research and medicine."

IMV Technologies, Protocol of Bioxcell with Fresh Semen, 1 page, 2000.

IMV Technologies, Protocol of Bioxcell with Frozen Semen, 2 pages, 2000.

Iwazumi, Y., et al., "Superovulation Using CIDR in Holstein Cows" J. of Reprod. Dev. vol. 40 (3) 1994, pp. 259-266.

Jakubiczka, S. et al. "A Bovine Homologue of the Human TSPY Gene," Genomics, 1993, vol. 17, No. 3, pp. 732-735.

Jarriage, R. "Age of Cows at First Calving in France." In: J.C. Taylor (Ed.) *The Early Calving of Heifers and its Impact on Beef Production*. 10. (1975).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Successful Gender Preselection in Farm Animals", Agricultural Biotechnology, p. 439-452. (1998).

Joseph, R. L. "Carcass composition and meat quality in once calved heifers." In: J.C. Taylor (Ed.) *The Early Calving of Heifers and its Impact on Beef Production*. 143. (1975).

Joseph, R. L. and J. P. Crowley, "Meat Quality of Once-Calved Heifers." Irish J. of Agric. Research 10:281. (1971).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kinder, J. E., et al. "Endocrine Basis for Puberty in Heifers and Ewes," J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes." Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long Term Estrogen Implants in Beef Heifers." J. Anim. Sci. 77:2886. (1999).

Kobata, Akira, "Structures and Functions of the Sugar Chains of Human Chorionic Gonadotropin", in *Glylcoprotein Hormones* Chin, W.W. and Boime, I., eds. Serene Symposia, Norwell. MA. p. 19-20. 1990.

Koch, R. M., et al., "Characterization of Biological Types of Cattle—Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Laster, D. B., "Factors Affecting Dystocia and Effects of Dystocia on Subsequent Reproduction in Beef-Cattle," J. Anim. Sci. 36:695. (1973).

Lightwave Electronics, "Xcyte," www.LightwaveElecronics.com.

Liu, Z., et al. "Survival of Bull Sperm Frozen at Different rates in Media Varying in Osmolarity." Cryobiology, vol. 27, 1998, pp. 219-230.

Lu, K. H, et al., "In Vitro Fertilization of Bovine Oocytes with Flow-Cytometrically Sorted and Unsorted Sperm from Different Bulls" Therio. abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Manni, Jeff. "To-Photon Excitation Expands the Capabilities of Laser-Scanning Microscopy,".

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matulis. R. J., "Growth and carcass characteristics of cull cows after different times-on-feed." J. Anim. Sci. 65:669. (1987).

Mauleon, P. "Recent research related to the physiology of puberty." In: J.C. Taylor (ed.) *The Early Calving of Heifers and its Impact on Beef Production*. (1975).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J, "The Flexibility of the Collagen Compartment of Muscle." Meat Sci. 36:79. (1994).

McLeod, John H., "The Axicon: A New type of Optical Element", Journal of the Optical Society of America. vol. 44 No. 8, Aug. 1954, Eastman Kodak Company, Hawk-Eye Works, Rochester, New York.

Meilgaard, M., et al., "Sensor Evaluation Techniques." CRC Press Inc., Boca Raton, FL. (1991).

Melamed et al, "An Historical Review of the Development of Flow Cytometers and Sorters", 1979. pp. 3-9.

Mendes Jr., J.O.B. "Effect of heparin on cleavage rates and embryo production with four bovine sperm prepration protocols" Theriogenology 60 (2003) 331-340.

Menke.E. A Volume Activated Cell Sorter Journal of Histo chemistry and Cyto Chemistry, 1977, vol. 25,No. 7, pp. 796-803.

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991,vol. 30 pp. 250-257.

Moe, P. W., "Energetics of Body Tissue Mobilization." J. of Dairy Sci. 54:548.

Moran, C., et al., "Puberty in Heifers—a Review." Animal Reproduction Sci. 18:167. (1989).

Morgan, J. B., et al., "National Beef Tenderness Survey," J. Anim. Sci. 69: 3274. (1991).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits," J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001(Su;;l. 1)64:156.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Patterson, D. J., et al., "Estrus Synchronization with an Oral Progestogen Prior to Superovulation of Postpartum Beef Cows" Therio. 48, 1025-33 (1997).

Penfold, L.M.et al., "Comparative Motility of X and Y Chromosome-Bearing Bovine Sperm Separated on the Basis of DNA Content". Mol. Reprod. and Develop. 1998, vol. 50.pp. 323-327.

Petit, M. "Early Calving in Suckling Herds." In: J.C. Taylor (ed.) *The Early Calving of Heifers and its Impact on Beef Production*, p. 151-176, (1975).

Picket B.W., et al., "Livestock Production Science," 1998.

Pinkel et al., "Flow Chambers and Sample Handling", Flow Cytometry: Instrumentation and Data Analysis, Van Dilla et al, (Eds.), 1985, pp. 77-128.

Pinkel, D., et al., "Sex Preselection in Mammals? Separation of Sperm Bearing the Y and "O" Chromosomes in the Vole Microlus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11, (1996).

Polge, et al, "Revival of Spermatozoa After Vitrification and Dehydration at Low Temperatures," Nature, 164:666 (1994).

Preza, C et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1996).

Prokofiev M.I. Regoulyatsia Razmnozhenia Seiskokhozyastvennykh Zhivotnykh. Leningrad, NAOUKA Publishing House, 1983, pp. 181-195.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle," J. Anim. Sci. 68:853. (1990).

Rathi, R. et al., "Evaluation of In Vitro Capacitation of Stallion Spermatoza", Biology of Reproduction 2001.vol. 65, pp. 462-470.

Recktenwald, Diether. "Cell Separation Methods and Applications," New York 1997.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance. Carcass, and Sensory Traits of Once-Calved Heifers" J. Anim. Sci. vol. 74 p. 2043-51 (199).

Riggs, B.A. "Integration of Early Weaning and Use of Sexed Semen in a Single-Calf Heifer System to Increase Value of Non-Replacement Heifers" MS Thesis, Colorado State University, Spring 2000.

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embryonic Development" Biology of Reproduction 55. 1012-1016 1996.

Romita. A. "Some Considerations on the Beef Situation in Italy." In: J.C. Taylor (ed.) *The Early Calving of Heifers and its impact on Beef Production*. 23. (1975).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Roy, J. H., "Rearing Dairy-Herd Replacements." Journal of the Society of Dairy Technology 31:73-79 (1978).

Rutter, L. M., et al., "Effect of Abomasal Infusion of Propionate on the GnRH-Induced Luteinizing Hormone Release in Prepuberal Heifers," J. Anim. Sci. 56:1167 (1983).

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71 (1998) abstr.

Seidel, G. E. Jr. "Cryopreservation of Equine Embryos" Veterinary Clinics of North America: Equine Practice vol. 12, No. 1, Apr. 1996.

Seidel, G. E. Jr. "Sexing Bovine Sperm" The AABP Proceedings—vol. 34.

Seidel, G. E. Jr, Sexing mammalian spermatozoa and embryos-state of the art Journal of Reproduction and Fertility Supp 54, 477-487 1999.

Seidel, G. E. Jr et al., "Current Status of Sexing Mammalian Spermatozoa," Society for Reproduction and feftiity, pp. 733-743, 2002.

Seidel, G. E. Jr., "Commercilizing Reproductive Biotechnology—The Approach used by XY, Inc.," Theriogenology, p. 5, 1999.

Seidel, G. E. Jr., et al, "Sexing Mammalian Sperm—Overview", Therio. 52: 1267-1272, (1999).

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females," J. Anim. Sci. 73:3304. (1995).

Shapiro. Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 Abstract.

Sharpe, Johnathan, Thesis; "An Introduction of Flow Cytometry", Ch. 2-2.2, 1997.

Sharpe, Johnathen, Thesis: "Gender Preselection-Principle Scientific Options," Ch. 3.4-3.4.8. 1997.

Sharpe, Johnathan, Thesis: "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shorthose, W. R. and P. V. Harris. "Effect of Animal Age on the Tenderness of Selected Beef Muscles." J. Food Sci. 55:1-. (1990).

Silbermann, M., "Hormones and Cartilage Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University, (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine.

Solsberry G.U., Van-Denmark N.L., Theory and practice of artificial cow insemination in USA, Moscow, KOLOS Publishing House, 1966, p. 346.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Spectra-Physics, The Solid State Laser Company, Vanguard 2000-HMO 532, www.specra-physics.com.

Spectra-Physics, The Solid State Laser Company, Vanguard 350-HMD 355, www.specra-physics.com.

Squires, E.L., "Procedures for Handling Frozen Equine Semen for Maximum Reproductive Efficiency". pp. 1, 39-41, 81-89.

Staigmiller, R.B. "Superovulation of Cattle with Equine Pituitary Extract and Porcine FSH" Theriogenology 37: 1091-1099 1992.

Stap J. et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.

Steel, N. L., "Cost Effectiveness of Utilizing Sexed-Semen in a Commercial Beef Cow Operation". MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periperturient Cow." Therio 10:269. (1978).

Stevenson, J. S., et al., "Detection of Estrus by Visual Observation and Radiotelemetry in Peripubertal, Estrus-Synchronized Beef Heifers" J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Swanson, E, W. "Future Research on Problems of Increasing Meat Production by Early Calving." In: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Tatum, J. D., et al., "Carcass Characteristics. Time on Feed and Cooked Beef Palatability Attributes." J. Anim. Sci. 50:833. (1980).

Thun, Rico, et al., Comparison of Biociphos-Plus® and TRIS-Egg Yolk Extender for Cryopreservation of Bull Semen; Theriogenology Symposium. Dec. 1999, vol. 52, #8.

*Time-Bandwidth Products "GE-100—XHP"*, www.tbsp.com, 2 pages, Jan. 2002.

Unruh. J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric. Marketing Serv., USDA, Washington, DC. (1997).

Van Dilla, Martin, "Overview of Flow Cytometry: Instrumentation and Data Analysis", Flow Cytometry Instrumentation and Data Analysis. Van Dilla et al. (Eds.), 1985, pp. 1-8.

Vincent, B.C., et al, "Carcass Characteristics and Meat Quality of Once-Calved Heifers." Canadian J. Anim. Sci. 71:311. (1991).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380, 1990.

Watson, "Recent Developments and Concepts in the Cryopreservvation of Spermatozoa and the Assessment of Their Post-Thawing Function," Reprod. Fertil. Dev. 7:871-891 (1995) Abstract.

Wheeler, T.L., et al., "Effect of Marbling Degree on Beef Palatability in Bos-taurus and Bos-indicus cattle." J. Anim. Sci. 72:3145. (1994).

Wickersham, E. W. and L. H. Schultz "Influence of Age at First Breeding on Growth, Reproduction, and Production of Well-Fed Holstein Heifers." J. Dairy Sci. 48:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, D. E. et al., "Mammal Species of the World", Smithsonian Institution Press, 1993, 1206 pp.

Wintzer et al.:"Krankheiten des Pferdes Ein Leitfaden fur Studium und Praxiz," 1982, nParey, Berlin Hamburg XP002281450.

Zhou, Hongwei, et al. "Research on and Development of Flow Cell Sorting Apparatuses," Gazette of Biophysics, vol. 13. ed. 3, 1997.

Hamamatsu, *"Photomultiplier Tubes,"* web page, http://www.optics.org/hamamatsu/pmt.html. Printed on Apr. 14, 2000 4.

Hermesmeyer, G.N, .et al, Effects of Lactation and Prenatal Androgenization on the Performance. Carcass Composition, and Longissimus muscle sensory characteristics of heifers in the single-calf heifer system. The Professional Animal Scientist 15: 14-23.

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Hollinshead, F.K. et al. "In vitro and in vivo assessment of functional capacity of flow cytometrically sorted ram spermatozoa after freezing and thawing." Reprod. Fertil. and Develop. 2003. vol. 15, pp. 351-359.

Hollinshead F. K. et al. "Production of lambs of predetermined sex after the insemination of ewes with low numbers of frozen-thawed sorted X- or Y-Chromosome-bearing spermatozoa", Reprod. Fertil. and Develop. 2002, vol. 14, pp. 503-506.

Hollinshead F. K. et al. "Sex-Sorting and Re-cryopreservation of Frozen-Thawed Ram Sperm for In Vitro Embryo Production" Theriogenology , vol. 59. (2003) pp. 209.

Dhali et al. Vitrification of Buffalo (*Bubalus bubalis*)Oocytes, Embryo Theriogenology vol. 53, 1295-1303 (2000).

Borini et al. Cryopreservation of Mature Oocytes: The use of a trypsin inhibitor enhances fertilization and obtained embryos rates, Fertil. Steril. (1997), vol. 68 (Suppl.).

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for In Vitro fertiliation and AI, Journal of Animal Science,vol. 77, Suppl 2/J, Day Sci. vol. 82, Suppl. Feb. 1999 pp. 213-220.

Peters D., The LLNL high-speed sorter: Design features,operational characteristics, and bioloical utility, Cyometry, 6:290-301 (1985).

Rens W., et al Slit-scan flow cytometry for consistent high resdolution DNA analysis of X- and Y-chromosome bearing sperm, Cytometry 25:191-199 (1996).

van Munster, E. B. Interferometry in fior to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection. Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluoresense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/lsrll.htm, pp. 14, May 11, 2004.

Saacke,R.G., Can Spermatozoa with abnormal heads gain access to the ovum in artificially inseminated super- and single-ovulating cattle?, Theriogenology 50:117-128, 1998.

Hawk, H.W., Gamete Tran port in the Superovulated Cow. Theriogenology: Jan. 1998 vol. 29 No. 1 pp. 125-142.

Biecher, S.R., et al. A new approach to immunological sexing of sperm, Theriogenology, 59, 1309-1321, 1999 vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen recepters (ER) α and β during early development of bovine fetal ovaries: The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Do Not Cite This One Yet—Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, (2006) pp. 15.

Habermann F. A., et al., Validation of sperm sexing in the cattle (*Bos taurus*) by dual colour flourescence in situ hybridization; J Anim Breed Genet. Apr. 2005; 122 Suppl 1:22-7 (Abstract only).

Johnson, L. A., Sexing mammalian sperm for production of offspring: the state-of-the-art: Animal Reproduction Science; 60-61 (2000) pp. 93-107.

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science. vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Bavister, B.D. et al., The effects of Sperm Extracts and Energy Sources on the Motility and Acromosome Reaction of hamster Spermatozoa in vitero; Biology of Reproduction 16, 228-237 (1997).

Fattouh, El-S.M. et al., Effect of Caffine on the Post-Thaw Motility of Buffalo Spermatozoa; Theriogenology, Jul. 1991, vol. 36 No. 1.

Pursley, J.R. et al., Reproductive Management of Lactating Dairy Cows Using Synchronization of Ovulation, 1997 J. Dairy Sci. 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Aminals: Journal of Ancrology, vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems: J. Dairy Sci. 87: (E.Suppl.): E120-E130; 2004 American Dairy Science Assoc.

Arathy D.S., et al., In vitro-derived embryo production with sexed and unsexed semen from different bulls; Reproduction Fertility and Development, vol. 16, Part 1/2, p. 253, 2004.

Dalton, J.C., et al., Effect of Time of Insemination on Number of Accessory Sperm, Fetilization Rate, and Embryo Quality in Nonlactating Dairy Cattle. J Dairy Sci. 84 2413-2418.

Dransfield, M.B.G., et al., Timing of Inseminatio for Dairy Cows Identified in Estrus by a Radiotelemetric Etrus Detection System. 1998 J Dairy Sci. 81: 1874-1882.

Maatje, K. et al. Predicting Optimal Time of Insemination in Cows that Show Visual Signs of Estrus by Estimating onset of Estrus with Pedometers.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci 81: 2139-2144.

Rozeboom, K. J. et al. Late Estrus or Metestrus Insemination After Estrual Inseminations Decreases Farrowing Rate and Litter Size in Swine J. Animal Sci. 1997. 75: 2323-2327.

Peeler, I. D. et al. Pregnancy Rates After Times AI of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy, first page only.

Lukaszewicz, M. et al. Attempts on freezing the Greylag (*Anser anser* L.) gander semen Animal Reproduction Science 80 (2004) 163-173, first page only.

Foote, R. H. et al. Sperm Numbers Inseminated in Daily Cattle and Nonreturn Rates Revisited 1997 J Dairy Science 80:3072-3076, first page only.

Conley, H.H. el at. Intensification by Intrauterine Devices of Sperm first Loss from the Sheep Uterus Biology of Reproduction 2, 401-407 (1970), first page only.

Chrenek, Peter et al. Fertilizing Capacity of Transgenic and Non-Transgenic Rabbit Spermatozoa after Heterospermic Insemination Bull Vet. Inst. Pulawy 49, 307-310, 2005, first page only.

Bakst, Murray R. Fate of Fluorescent Stained Sperm following Insemination: New Light on Ovicucal Sperm Transport and Storage in the Turkey, first page only.

Nikkei Biotech, Supplement, Latest Information of Biological Instruments and Reagents, 1988, pp. 93-94.

Hollinshead, F.K. et al , Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Koh-ichi Hamano, et al., Gender Preselection in Cattle with Intracytoplasmically injected, flow cytometrically sorted sperm heads, Biology of Reporduction 60, 1194-1197 (1990).

Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

* cited by examiner

LOW PRESSURE SPERM CELL SEPARATION SYSTEM

This application is the United States National Stage of International Application No. PCT/US2003/024460, filed Aug. 1, 2003 which claims the benefit of U.S. Provisional Patent Application No. 60/400,971, filed Aug. 1, 2002, each hereby incorporated by reference herein.

I. TECHNICAL FIELD

Sperm cell insemination samples having selectably controlled sperm cell fertility characteristics produced through entrainment in a fluid stream having correspondingly selectably adjustable flow characteristics and methods of assessing comparative of sperm cell insemination sample fertility.

II. BACKGROUND

Pre-selection of sex has been accomplished in many species of livestock following the development of safe and reliable methods of separating sperm cells into enriched X chromosome bearing and Y chromosome bearing populations. See for example methods and apparatus disclosed by WO 00/06193; WO 02/043574; WO 01/85913; WO 99/33956; WO 01/40765; WO 98/34094; WO 99/42810; WO 02/043486.

A significant problem with sex selected sperm cells may be that separation of sperm cells at rates sufficient to produce sex selected insemination samples or sex selected inseminates which are viable or sufficiently fertile for commercial application by conventional technology has necessitated increasing fluid stream pressure of flow cytometers or flow sort instruments to about 50 pounds per square inch. With respect to sperm cells of many species of mammals entrained in fluid streams having flow characteristics resulting from this application of pressure the viability, motility, or other fertility characteristics altered.

Another significant problem with sex selected sperm cell inseminates or sex selected sperm cell insemination samples can be the vast difference in sperm cell fertility characteristics which can vary greatly between samples. As such, success of artificial insemination performed under substantially identical conditions can result in correspondingly different pregnancy rates.

Another significant problem with existing sperm cell sex selection technology can be the lack of an assay from which fertility of sex selected sperm cells can be compared directly in-vivo (for example, in conjunction with artificial insemination procedures) and in-vitro (for example, in conjunction with IVF procedures).

The instant invention addresses the variety of problems associated with reduced sperm cell fertility spermatozoa that have been separated into enriched X-chromosome bearing and Y-chromosome bearing populations and the lack of heterospermatic assays to compare function and fertility of separated or sorted sperm cells, and in particular flow sorted sperm cells.

III. DISCLOSURE OF THE INVENTION

Accordingly, the broad object of the invention provides devices and methods of using such devices to control sperm cell fertility characteristics of sperm cells isolated from semen obtained from a male of species of mammal, such as motility, viability, fertilization rate, cleavage rate, blastocyst rate, or the like.

Providing controlled sperm cell fertility in accordance with the invention can be achieved with the sperm cells obtained from numerous and varied species of mammals, including without limitation, mammals selected from the group consisting of a bovine species of mammal, an equine species of mammal, an ovine species of mammal, a canine species of mammal, a feline species of mammal, a swine species of mammal, a marine species of mammal, a deer species of mammal, a primate species of mammal, a goat species of mammal, or a species of mammal listed by Wilson, D. E. and Reeder, D. M., *Mammal Species of the World*, Smithsonian Institution Press, (1993), hereby incorporated by reference herein.

With respect to certain embodiments of the invention, controlled sperm cell fertility characteristics comprises affirmative selection of fertility characteristics in advance of isolating sperm cells from the semen of the male of the species of mammal and application of the invention to alter sperm cell fertility characteristics to provide the fertility characteristics desired. With respect to other embodiments of the invention, sperm cell treatment conditions are selected within a broader range of sperm cell treatment conditions that can be used treat sperm cells of a particular species of mammal to obtain sperm cells having controlled fertility characteristics. Controlled fertility characteristics can comprise a desired proportion of motile sperm cells, intact acrosomes, viable sperm cells within a population of treated sperm cells; or can comprise a desired cleavage rate of oocytes or rate of blastocyst formation when treated sperm cells are utilized to fertilize oocytes in vitro; or can comprise a desired pregnancy rate or sex ratio of offspring when treated sperm cells are utilized for artificial insemination. With respect to certain embodiments of the invention, a greater proportion of motile sperm cells, a greater proportion of viable sperm cells, a greater proportion of intact acrosomes, or a greater number of fertile sperm cells within a treated sperm cell population can be achieved compared to conventional treatment of the same of sperm cell population. Certain embodiments of the invention allow provision of sperm cells having controlled fertility characteristics which are not substantially different than, or are substantially comparable to, the fertility characteristics of sperm cells in fresh ejaculated semen. In other instances, application of certain embodiments of the invention can if desired result in sperm cells having controlled fertility characteristics which are substantially different than those of sperm cells of fresh ejaculated semen. In particular, certain embodiments of the invention can be used to provide bovine sperm cells having controlled fertility characteristics or can be used to provide equine sperm cells having controlled fertility characteristics, which if desired can be provided with fertility characteristics substantially comparable to the fertility characteristics of bovine sperm cells or equine sperm cells within freshly ejaculated bovine or equine semen.

Another broad object of the invention can be to provide sperm cell insemination samples having controlled sperm cell fertility characteristics, such sperm cell insemination samples, without limitation, can be configured for artificial insemination of a female of a species of mammal, in vitro fertilization of oocytes, or intracytoplasmic injection of sperm cells, or the like.

Another broad object of the invention can be to provide methods of sex selecting sperm cells that can provide affirmative control of sperm cell fertility characteristics such as motility, viability, fertilization rate, cleavage rate, blastocyst rate, or the like. One aspect of this broad object of the invention can be to provide flow cytometry or cell sorting devices or methods of flow cytometry or cell sorting which allows affirmative control of the fertility characteristics of sex selected sperm cells.

Another object of the invention can be to provide sex selected bovine sperm cell insemination samples having controlled sperm cell fertility characteristics configured for artificial insemination of a female of a bovine species of mammal containing between about 100,000 and about 3,000,000 sex selected bovine sperm cells having controlled sperm cell fertility characteristics.

Another object of the invention can be to provide sex selected equine sperm cell insemination samples having controlled sperm cell fertility characteristics configured for artificial insemination of a female of an equine species of mammal containing between about 5,000,000 and about 50,000,000 sex selected bovine sperm cells having controlled sperm cell fertility characteristics.

Another significant object of the invention can be to provide devices or methods of maintaining controlled sperm cell fertility characteristics of sperm cells with respect to processing of sperm cells, storage of sperm cells, or use of sperm cells, including, but not limited to, insemination of female mammal(s) or fertilization of oocyte(s).

Another significant object of the invention can be to provide methods of artificially inseminating females of a species of mammal with sperm cell insemination samples having controlled sperm cell fertility characteristics. With respect to certain embodiments of the invention, methods of insemination with a low or reduced number of sperm cells having controlled fertility characteristics compared to the usual number or typical number of sperm cells used in such artificial insemination procedures whether or not such sperm cells are separated into enriched X chromosome bearing or Y chromosome bearing sperm cell populations.

Another broad object of the invention can be to provide a method of assessing comparative fertility of sperm cell populations. Certain embodiments of the invention provide a method of assessing comparative fertility of sperm cells from different males of a species of mammal when sperm cells from each male are exposed to substantially the same flow cytometric treatment. Other embodiments of the invention provide a method of assessing comparative fertility of sperm cells from the same male of a species of mammal which are exposed to different flow cytometric treatments. Certain embodiments of the invention provide methods of showing comparative fertility of sperm cells having controlled fertility characteristics.

Naturally, further significant objects of the invention are made clear in the proceeding description of the invention.

IV. BRIEF DESCRIPTION OF DRAWINGS

V. MODE(S) FOR CARRYING OUT THE INVENTION

A semen or sperm cell process system to maintain, enhance, assay, test, or determine the biological, chemical, physical, physiological, or functional attributes of sperm cells within the context of various collecting, handling, storage, transportation, separation, or insemination procedures.

An embodiment of the invention can comprise obtaining a sperm cells from a species of mammal as broadly defined above. The sperm cells can then be entrained in a fluid stream having flow characteristics. The fluid stream within a conduit has flow characteristics influenced by the rheological properties of the fluid stream, the configuration or geometries of the conduit in which the fluid stream flows, as well as external forces applied to the fluid stream such as hydrostatic pressure, oscillatory vibrations, piezoelectric vibrations, oscillations in heat, or the like.

Importantly, these flow characteristics of the fluid stream contribute to the amount of pressure required to move fluid within the conduit. As a non-limiting example, in flow cytometry fluid moves within a relatively large cross sectional area and then within a relatively small cross sectional area past an analysis interface to a final collection point.

This type of configuration or geometry along with rheologic properties of the fluid stream can create localized forces such as compressive forces, sheer forces, or the like, which can have influence the physical integrity of particles such as sperm cells entrained in the fluid stream.

Figure 1:
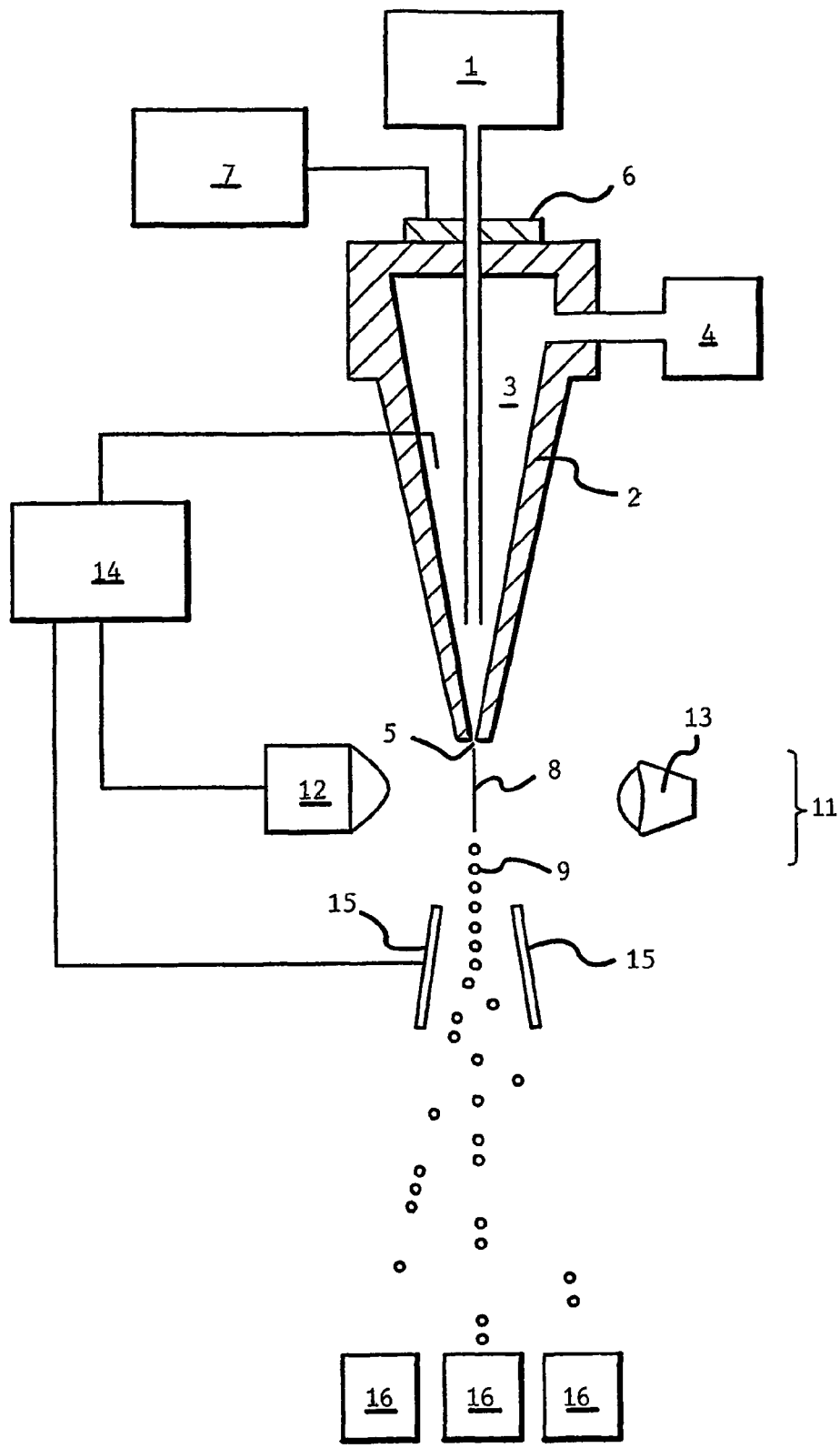
FIG. 1 is a schematic diagram of a sorter system according to a flow cytometer separation technique for the present invention.

With respect to those embodiment of the invention which include components of or steps involving flow cytometry or cell sorting as a means to analyze, separate based upon a sperm cell characteristic, sex select, or other wise process sperm cells, a conceptual non-limiting flow cytometer or cell sort instrument is shown by FIG. 1.

A flow cytometer or cell sort instrument includes all or a portion of the components shown by FIG. 1 including with out limitation, a sperm cell source (1) which acts to establish or supply sperm cells to analyze, separate, control fertility characteristics, or be otherwise treated.

Sperm cells are deposited within a nozzle (2) in a manner such that sperm cells are surrounded by a sheath fluid (3). Any sheath fluid compatible with the flow cytometer or flow sort instrument and which provides an acceptable environment for sperm cells during flow analysis or processing can be utilized with the invention, including without limitation, sheath fluids which contain, individually or in various combinations, a phosphate buffered saline, a citrate solution (such as a 2.9% sodium citrate solution), or a HEPES buffered solution.

The sheath fluid (3) is usually supplied by some sheath fluid source (4) so that as the sperm cell source (1) supplies sperm cells, the sheath fluid (3) is concurrently fed through the nozzle (2). In this manner, the sheath fluid (3) forms a sheath fluid environment for the cells. Since the various fluids are provided to the flow cytometer at some pressure, they flow out of nozzle (2) and at the nozzle orifice (5).

By providing some type of oscillator (6) which may be very precisely controlled through an oscillator control (7), pressure waves may be established within the nozzle (2) and transmitted to the sheath fluid exiting the nozzle (2) at nozzle orifice (5). Since the oscillator (6) thus acts upon the sheath fluid (3), the stream (8) exiting the nozzle orifice (5) eventually and regularly forms drops (9). Because the cells are surrounded by a sheath fluid environment, the drops (9) may contain within them individually isolated sperm cells (10).

Since the droplets (9) generally contain isolated sperm cells (10), the flow cytometer or cell sorter instrument can distinguish between and separate droplets based upon a distinguishing sperm cell characteristic(s) of the sperm cell contained within a droplet (9). This is accomplished through a sperm cell sensing system (11). The sperm cell sensing system involves at least some type of detector (12) which responds to sperm cells contained within each droplet (9).

One type of sperm cell sensing system (11) is as discussed at length in U.S. Pat. No. 5,135,759 to Johnson, hereby incorporated by reference herein. As the Johnson patent explains for sperm cells, the cell sensing system (11) may cause an action depending upon the relative presence or relative absence of a particular dye which may be excited by some stimulant such as the beam of a laser (13). While each type of sperm cell can be stained with a dye, the differing length of the X-chromosome and the Y-chromosome causes different levels of staining. Thus, by sensing the degree of dye present in each sperm cells it is possible to discriminate between X-chromosome bearing sperm and Y-chromosome bearing sperm by their differing emission levels. Alternate optics, detection and sperm cell analysis systems are known which can also be used in accordance with the invention and it is intended that the description provided by the Johnson patent is for illustrative purposes so that the numerous and varied uses of the invention can be understood. See also, WO 01/85913, hereby incorporated by reference herein.

In order to achieve the ultimate separation and isolation of the appropriate cells in a flow cytometer or cell sort instrument separation technique, the signals received by sensor (12) are fed to some type of sorter discrimination system (14) which very rapidly makes the decision and can differentially charge each droplet (9) based upon whether the desired cell does or does not exist within that droplet (9). In this manner the sorter discrimination system (14) acts to permit the electrostatic deflection plates (15) to deflect droplets (9) based on whether or not they contain the a sperm cell having certain sperm cell characteristics. As a result, the flow cytometer or cell sorter instrument acts to separate the cells by causing them to land in one or more collection containers (16). Thus by sensing some property of the sperm cells the flow cytometer or cell sorter instrument can discriminate between cells based on a particular characteristic and place them in the appropriate collection container (16). In certain flow cytometers or cell sorter instruments, the X-bearing sperm droplets are charged positively and thus deflect in one direction, the Y-bearing sperm droplets are charged negatively and thus deflect the other way, and the wasted stream (that is unsortable cells) is uncharged and thus is collected in an undeflected stream into a suction tube or the like.

Figure 2:
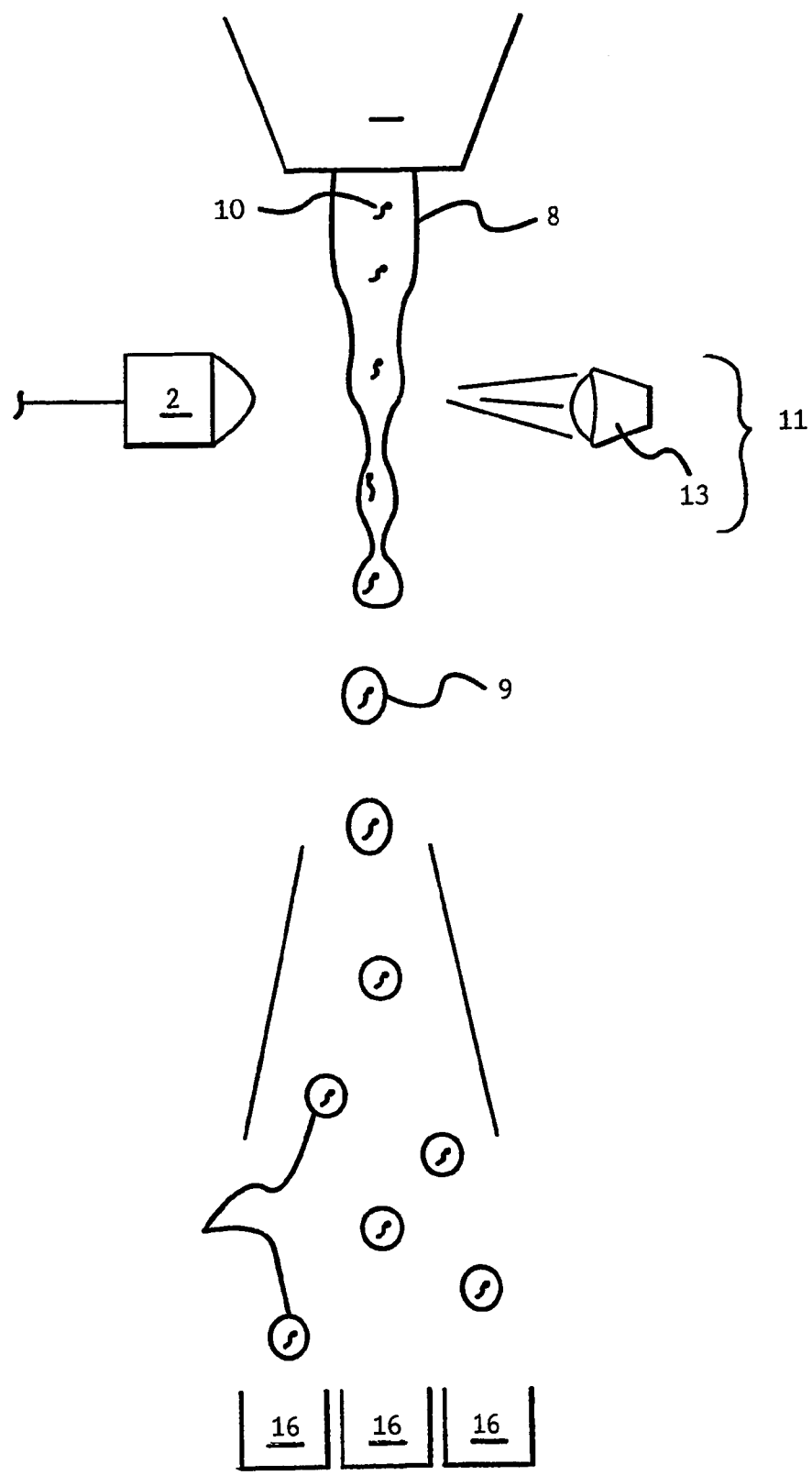
FIG. 2 is a diagram of the entrained cells in the free fall area of a typical flow cytometer.

Now referring primarily to FIG. 2, the process can be even further understood. As shown in that figure, the nozzle (2) emits a stream (8) which because of the oscillator (7) (not shown in FIG. 2) forms drops (9). Since the cell source (1) (not shown in FIG. 2) may supply sperm cells (10) which as described by Johnson can be stained (or in certain embodiments of the invention unstained as when using DIC technology), the light emission generated by the beam generated by laser (or illumination source when using DIC technology) (13) incident upon the dye (the sperm head when DIC technology is utilized) is differentially determined by sensor (12) so that the existence or nonexistence of a charge on each drop (9) as it separates from stream (8) can be controlled by the flow cytometer. This control results in positively charged, negatively charged, and uncharged drops (9) based upon their content. As shown in FIG. 2, certain drops are shown as deflected drops (17). These deflected drops (17) are those containing sperm cells (10) which can be one or the other sex. They are then deposited in the appropriate collector (16) thereby generating a population of sex selected sperm cells.

Whether the fluid stream occurs within the context of a flow cytometer, cell sorter, or other device which entrains sperm cells within a fluid stream, the flow characteristics of the stream can be characterized and adjustment means for altering flow characteristics of the fluid stream can be introduced to increase or decrease forces such as compressive forces, sheer forces, or the like, such that particles entrained in the fluid stream can be physically, physiologically, functionally, or mechanically altered.

As such a selectably adjustable range of fluid stream characteristics for a flow path can be generated using the adjustment means and can be expressed as an incremental measure. For example, alteration of fluid stream characteristics within a flow cytometer or cell sort instrument context can be incrementally adjusted and measured in pounds per square inch and typically allow the incremental increase or decrease in fluid stream pressure between about 20 pounds per square inch and 100 pounds per square inch with a commensurate increase or decrease in fluid stream or sheath fluid velocity.

In accordance with certain embodiments of the invention, sperm cells of a particular species of mammal are entrained in a fluid stream having adjustable fluid stream flow characteristics. Fluid stream flow characteristics are then selectably adjusted over an incrementally measured range in which the entrained sperm cells remain viable. Sperm cell fertility characteristics are then assessed for each of a plurality of sperm cell samples taken in correspondence to each of a plurality of flow characteristics generated within the measured range.

Subsequently, sperm cell fertility characteristics with respect to sperm cells from a species of mammal or individual members of a species of mammal can be controlled and sperm cell insemination samples can be generated having the desired sperm cell fertility characteristics.

For example, sperm cells from each of six bulls were stained with 125 μm Hoechst 33342 for 45 min at 34° C., and bulk-sorted (passed through a flow cytometer or cell sorter instrument without sorting into subpopulations) or sorted with a flow cytometer having a nozzle with an internal diameter of 70 μm into X-chromosome bearing or Y-chromosome bearing (or both) populations at about 95% accuracy with the fluid stream having a pressure of at 30 pound per square inch, 40 psi, or 50 psi. Lowering the fluid stream pressure from 50 psi to 30 psi reduced sorting rate by only 2 to 3%.

The sperm cells were subsequently cooled to 5° C. and concentrated by centrifugation, loaded into 0.25 ml straws with about $2 \times 10^6$ total sperm cells per 100 μl column, and frozen using a vapor freezing method along with unsorted controls. The sperm cells in the straws were subsequently thawed.

Sperm cells were then evaluated with respect to various sperm cell fertility characteristics blindly by two observers at 30 and 120 min post-thaw for progressive motility, as well as by flow cytometry 105 min post-thaw, for percent live sperm cells by PI stain, and by CASA analysis 120 min post-thaw using the Hamilton Thorne system. The entire procedure was twice replicated.

Factorial ANOVA indicated that both bull and pressure effects were significant (P<0.005, Table I).

TABLE 1

Responses of sperm post-thaw to different system pressures during sorting.[a]

| Response | Pressure (psi) | | | Unsorted Control |
|---|---|---|---|---|
| | 50 | 40 | 30 | |
| 30 min motility (%) | 44.7 | 48.6 | 49.6 | 52.1 |
| 120 min motility (%) | 34.5 | 40.8 | 42.7 | 40.8 |
| Live sperm (%) | 51.7 | 55.7 | 57.8 | 58.5 |
| CASA total motility (%) | 25.1 | 37.2 | 40.9 | 34.8 |
| CASA ALH* | 6.0 | 7.6 | 7.8 | 8.8 |

[a]All statistically significant, P < .005.
*Amplitude of lateral head displacement.

Higher numbers mean less stiff and more normal motility. There were typical differences among bulls in all responses. However, the bull by treatment interactions were small with one exception, meaning findings apply similarly to most bulls in the population. The flow characteristics of the fluid stream adjusted incrementally to increase pressure affected substantially all sperm cell fertility characteristics measured, however, only highly statistically significant ones are in Table 1.

As can be understood, there was significant change in sperm cell fertility characteristics between sperm cell samples taken at about 50 psi and at about 40 psi, and then a much smaller change between about 40 psi and about 30 psi, indicating that the effect on sperm cell fertility characteristics can not be assumed linear. For bovine sperm cells exposed to the flow characteristics described at 30 psi, sperm cell fertility characteristics were substantially the same as nonsorted controls or comparable to nonsorted controls, and for a few responses better, if sperm cells are to be used for insemination or artificial insemination of females of the bovine species. Similar procedures were conducted with sperm cells obtained from stallions with similar results and conclusions.

Sperm cell fertility characteristics can be controlled and with respect to sperm cells obtained from mammals. For most species of mammals altering fluid stream characteristics to incrementally reduce fluid stream pressure, whether in the context of flow cytometry or otherwise, can result in a graded series of corresponding sperm cell samples having altered sperm cell fertility characteristics which may be used for a variety of procedures including artificial insemination, in vitro fertilization, or intracytoplasmic injection as described below.

The invention provides a alternate tests to assess binomial responses such as pregnant/not pregnant, which typically require large numbers of animals per treatment to obtain statistical significance unless treatment differences are fairly large. One embodiment of the invention which can amplify differences in sperm cell fertility characteristics of sex selected sperm due to treatment differences comprises competitive, or heterospermic, fertilization, mixing sperm of different treatments or males before insemination, and determining the proportion of embryos, fetuses or offspring derived from each male or treatment.

For example, fertility after sex selection of sperm cells by flow cytometry or by cell sorting for DNA content at two different fluid stream pressures can be assessed using heterospermic insemination using sex as the genetic marker. Sperm cells from each of two bulls was sorted into X-chromosome bearing or Y-chromosome populations, or both, at about 95% accuracy with the fluid stream pressure adjusted to either 30 psi or 50 psi. After concentrating sperm cells post-sort by centrifugation, $1 \times 10^6$ X-chromosome bearing sperm cells sorted at 30 psi were placed in 0.25-mL straws with $1 \times 10^6$ Y-chromosome bearing sperm cells sorted at 50 psi for each bull, as well as the converse in other straws: $1 \times 10^6$ Y-sperm at 30 psi plus $1 \times 10^6$ X-sperm at 50 psi. These sperm cells, along with unsorted controls, were then frozen, thawed some months later, and inseminated into the body of the uterus of 85 Holstein heifers either 12 or 24 h after observed estrus with subgroups balanced across two inseminators.

Two months post-insemination, 81% of the 43 heifers becoming pregnant had fetuses of the sex (determined by ultrasound) corresponding to the sex of sperm processed at 30 psi. This differed from the 50:50 sex ratio expected (P<0.01), if there was no difference in sperm cell fertility characteristics of sperm cells sorted at the two pressures. The pregnancy rate with sex selected sperm at $2 \times 10^6$ sperm per dose was 51% (43/85); this was similar to the controls of $20 \times 10^6$ unsexed sperm per dose from the same ejaculates, 39% (9/23).

Another embodiment of the invention provides a method altering the cleavage rate and rate of blastocyst formation using sperm cells having controlled sperm cell fertility characteristics. Two bovine sperm cell samples each having controlled fertility characteristics were generated by flow sorting bovine sperm cells at 40 psi and 50 psi respectively. Dose response of sperm cell concentration in the fertilization medium was conducted with X-chromosome bearing sperm cells and Y-chromosome bearing sperm cells from each sperm cell sample. Thus, a multifactorial procedure comprising 2 fluid stream pressures, 3 sperm cell concentrations (1, 0.33 and $0.11 \times 10^6$ sperm/ml), 6 bulls and 2 sexes can be conducted.

About 2,000 oocytes were aspirated from about 2 mm to about 8 mm follicles from slaughterhouse ovaries. Chemically defined media (CDM) were used throughout as described by Journal of Animal Sciences, 78:152-157 (2000), hereby incorporated by reference herein. Maturation took place in M-CDM supplemented with 0.5% FAF-BSA, 15 ng/ml NIDDK-oFSH-20, 1 µg/ml USDA-LH-B-5, 0.1 µg/ml $E_2$, 50 ng/µl EGF and 0.1 mM cysteamine for 23 h at 38.8° C. and 5% $CO_2$ in air. Sorted sperm cells frozen with $2 \times 10^6$ cells per straw were thawed and centrifuged at 400 g through 2 ml 45% and 2 ml 90% Percoll gradients for 20 min. Then the supernatant was discarded and 2 ml of FCDM supplemented with 0.5% FAF-BSA, 2 mM caffeine and 0.02% heparin was added to the sperm pellet and centrifuged at 500 g for 5 min. The supernatant was discarded leaving approximately 50 µl of sperm suspension. Matured oocytes were washed once in FCDM and transferred in groups of 15 in 5 µl into 25-µl drops of FCDM under mineral oil. Fertilization took place by adding 10 µl of sperm suspension per drop for 18 h at 38.8° C., 5% $CO_2$ in air. Presumptive zygotes were cultured in CDM1 for 2 d and CDM2 for 4.5 d at 38.5° C., 5% $O_2$, 5% $CO_2$ and 90% $N_2$. On day 7.5, blastocyst development was evaluated: Quality 1 to 4 (1 being excellent and 4 being poor) and stage of development, 6 to 8 (6 full, 6.5 expanding, 7 expanded, 7.5 hatching and 8 hatched blastocysts). Data (Table 1) were analyzed by ANOVA and first deviation after arc sin transformation.

Cleavage (53.6 and 43.6%) and blastocyst (18.2 and 14.7%) rates were higher for procedures utilizing sperm cells having controlled sperm cell characteristics obtained at about 40 psi than at about 50 psi (P<0.01). There was no interaction between dose and pressure; therefore, there was a similar advantage to lower pressure at each sperm concentration. A clear dose response of sperm cell concentration for cleavage and blastocyst production was found (Table 2). Also, there were large differences among bulls (P<0.01) for both responses, and there was a bull x dose interaction (P<0.01) for % cleaved. The data indicate that the sperm dose should be $>1.0 \times 10^6$/ml for some bulls. Embryo quality was higher (P<0.01) for Y-sperm than X-sperm (1.12 vs 1.57). Others have noted this for IVF embryos when embryos were sexed, and this effect now is confirmed with sexed sperm.

TABLE 2

Cleavage (%, C) and blastocysts (%, B) per oocyte data presented by bull.

|  | Bull | | | | | | | | | | | | |
|---|---|---|---|---|---|---|---|---|---|---|---|---|---|
|  | H023 | | H024 | | H025 | | H026 | | H027 | | H028 | | Avg |
| Sperm conc. ($10^6$) | C | B | C | B | C | B | C | B | C | B | C | B | C | B |
| 0.11 | 18 | 1 | 6 | 1 | 4 | 11 | 36 | 15 | 20 | 7 | 54 | 15 | $30^a$ | $8^a$ |
| 0.33 | 44 | 4 | 7 | 2 | 72 | 31 | 62 | 21 | 29 | 11 | 68 | 18 | $47^b$ | $14^b$ |
| 1.0 | 56 | 18 | 35 | 14 | 85 | 43 | 83 | 34 | 72 | 27 | 85 | 29 | $69^c$ | $28^c$ |

[a,b,c]Values without common superscripts within groups differ, P < 0.01.

**Fertility of sorted sperm has been low compared to unsorted control sperm, due partly to mechanical damage during sperm sorting by flow cytometry. Lowering system pressure improved both sperm quality and fertility in IVF. The present study evaluated the effect of system pressure during sperm sorting and extended maturation of oocytes on development of embryos after ICSI. Sperm from each of 3 bulls were stained with 125 µM Hoechst 33342 for 45 min at 34° C., sorted into X- and Y-chromosome bearing populations at 95% accuracy with the pressure of SX MoFlo® sorters at 40 or 50 psi, and then cryopreserved. Fifty bovine oocytes obtained from slaughterhouse ovaries were placed per well with 1 ml of CDM1 supplemented with 0.5% FAF-BSA, 2 mM glucose, 50 ng/ml EGF, 15 ng/ml NIDDK-oFSH-20, 1 µg/ml USDA-LH-B-5, 1 µg/ml E2 and 0.1 mM cysteamine, and then matured for 24 h or 30 h at 38.5° C., 5% $CO_2$ in air. Cumulus cells of matured oocytes were removed by vortexing, and oocytes with a polar body were selected. Motile sperm from sorted frozen-thawed semen were recovered by centrifugation through 2 ml each of 45 and 90% Percoll, and the concentration adjusted to $4 \times 10^6$/ml. Matured oocytes were divided into two injection groups, ICSI and sham injection using a Piezo injection system. The outer diameter of the sperm injection pipette was 8-10 µm. All manipulations were performed at room temperature (24-25° C.). After injection, oocytes were activated with 5 µM ionomycin for 4 min, cultured in 50 µl of CDM1 at 38.5° C. under 5% $CO_2$, 5% $O_2$ and 90% $N_2$, and assessed for cleavage at 72 h post-injection. Uncleaved oocytes from ICSI and sham injected groups were stained with orcein and evaluated for fertilization status. Cleaved embryos were further cultured and blastocyst development was evaluated on day 7.5 after injection. Data were subjected to ANOVA; the arc sin transformation was used for percentage data.

With 24 h matured oocytes, there were no differences (P>0.1) between sperm sorted at 40 versus 50 psi for cleavage or blastocyst rates, nor was there pressure x bull interaction. There were significant effects of bulls for all responses studied (P<0.05). When injected with sperm sorted at 40 psi, oocytes matured for 30 h resulted in a higher cleavage rate than 24 h matured oocytes (22.9 versus 12.2%, P<0.05), with no difference (P>0.1) in blastocyst rate. Overall blastocyst development was higher in ICSI than in sham injection (7.5 versus 1.3%, P<0.05). When uncleaved oocytes from 24 h maturation were evaluated for fertilization status, ICSI showed higher percentage with 2 polar bodies and/or decondensed sperm compared to sham injection (15.7 versus 1.7%, P<0.05). With 30 h matured oocytes there was no difference in fertilization status between those two groups. We conclude that there was no difference in cleavage or development to blastocysts after ICSI using motile sperm that had been sorted at 40 vs 50 psi.

In another embodiment of the invention, heterospermic insemination using sex as the genetic marker can be used to rank fertility of males and to rank fertility of sperm treatments not involving sperm sexing. Current in vitro tests of sperm function are not highly correlated with male fertility, and homospermic inseminations require hundreds of inseminations per treatment to obtain accurate fertility data. Heterospermic insemination, mixing the sperm of two or more males, provides an accurate estimation of relative fertility in most species examined.

Frozen, flow-sorted sperm from 4 groups of 4 bulls were thawed and inseminated into heifers 12 h or 24 h following onset of estrus in all combinations of 3 bulls within groups (ABC, ABD, ACD, BCD). Equal numbers of progressively motile sperm were inseminated from each bull, totaling 600,000 motile sperm post-thaw. Half of each inseminate was deposited into each uterine horn. Embryos were collected nonsurgically 14.5 to 20 days following estrus. Collections yielded 165 elongating embryos from 332 heifers (48%). Polymorphic DNA markers were used to genotype embryos to determine the sire of each embryo biopsy. After genyotyping, 118 of the 165 embryos could be assigned a specific sire. Heterospermic indices for ranking each bull group were calculated using the maximum likelihood analysis theorem. Each bull within groups was ranked based on these indices (Table 3). In group 1, the fertility of the poorest bull was significantly lower (P<0.05) than two other bulls. In group 2, the dominant bull had the highest index (P<0.05). Similar distinctions could be made in groups 3 and 4. However, in three of the groups the fertility of some bulls was not clearly high or low (P>0.05).

TABLE 3

Heterospermic indices ± SE for individual bulls within groups.

| Group 1 | Group 2 | Group 3 | Group 4 |
|---|---|---|---|
| $1.47 \pm .41^a$ | $2.43 \pm .43^a$ | $1.68 \pm .44^a$ | $0.92 \pm .36^{a,b}$ |
| $0.44 \pm .27^{a,b}$ | $0.22 \pm .15^b$ | $1.09 \pm .39^{a,b}$ | $0.46 \pm .20^a$ |
| $1.84 \pm .46^a$ | $0.90 \pm .35^b$ | $0.83 \pm .31^{a,b}$ | $2.02 \pm .40^b$ |
| $0.25 \pm .17^b$ | $0.45 \pm .23^b$ | $0.40 \pm .22^b$ | $0.59 \pm .24^a$ |

[a,b]Indices without common superscripts differ, P < 0.05.

With these procedures, an average of 30 genotyped embryos per group of 4 bulls enabled detection of bulls with clearly differing fertility. Sperm treatments also could be evaluated with this technique. This in vivo test requiring few females rapidly provides information concerning which bulls have relatively high or low fertility.

The population of calves obtained by artificial insemination of females with sex selected sperm cells in accordance with the invention are virtually identical to controls using unsex selected sperm cells. Furthermore, artificial insemination of females with sex selected sperm resulted in approximately 90% of calves of the planned sex. As described above, sperm cells can be sex selected on the basis of DNA content by flow cytometry or by cell sorting after staining with H33342. The sex selected sperm cells can then be cryopreserved as described in Theriogenology, 52:1375 "Cryopreservation of Flow-Sorted Bovine Spermatozoa", hereby incorporated by reference herein.

Estrus can be synchronized in heifers and cows of various beef and dairy breeds, either by feeding 0.5 mg melengestrol acetate (MGA) daily for 14 d followed by 25 mg prostaglandin $F_{0.2}$ ($PGF_{0.2}$) im 17 to 19 d later or injection of 25 mg $PGF_{0.2}$ im at 12-d intervals. Insemination with either frozen-thawed sex selected insemination samples or frozen-thawed sperm from the same ejaculate have been accomplished at either 12 hours or 24 hours after initial observation of estrus. For each breeding group, about ⅔ of the inseminations were with sexed sperm while control sperm were used in the remainder. Pregnancy and fetal sex were diagnosed by ultrasound 2 months later.

Cattle were managed at 13 farms through calving and weaning under differing levels of management (N=49 to 228 per farm). Data collected included gestation length, birth weight, calving ease (1=normal to 4=Caesarian), weaning weight, neonatal deaths, and deaths from birth to weaning. Not all farms recorded birth and weaning weights. Data were subjected to factorial analysis of variance with factors: management groups, sorted versus control sperm, and sex of calves. The arc sin transformation was used for percentage data. Least-square means are in Table 4.

TABLE 4

Calving results from sexed and control calves

| Treatment | N | Gestation length (d) | Neonatal death (%) | Calving ease | Birth weight (kg) | Live at weaning (%) | Weaning weight (kg) |
|---|---|---|---|---|---|---|---|
| Sexed[a] | 574 | 279 | 3.9 | 1.31 | 34.3 | 92.0 | 239 |
| Control | 385 | 279 | 5.9 | 1.30 | 34.1 | 88.9 | 239 |

[a]No significant differences (P > 0.1) for any response.

There were no differences (P>0.1) between calves from sexed versus control groups for any response studied, nor were there significant interactions. There were significant effects of management groups for all responses studied (P<0.001 for all except % alive at weaning, P<0.02). Also, there were significant differences (all P<0.001) between female and male calves for birth weight: 32.2 and 35.5 kg; weaning weight: 232 and 246 kg; calving difficulty: 1.20 and 1.42; and gestation length: 278 and 280 d.

The sex ratio of the control calves was 51.0% males (N=382). X sort sperm resulted in 87.7% females, while the Y sort sperm produced 93.6% males (N=94). A few calves that were dead at birth did not have sex recorded and are not included. The recent development of flow cytometric separation of stallion spermatozoa has resulted in the production of normal foals with preselected sex. (Lindsey A. C., Morris L. H., Allen W. R., Schenk J. L., Squires E. L., Bruemmer J. E. Equine vet. J. 2002, 34: 128-132). For this technology to be accessible, semen will be transported from the flow cytometer to the mare. This study examined the longevity and acrosome status of fresh stallion spermatozoa after sex preselection. Three ejaculates from each of 7 stallions were collected by artificial vagina and shipped to the laboratory at 20° C. for 2-6 h in a skim milk-glucose extender (1:1 v/v). The semen was centrifuged at 400 g for 10 min and the seminal plasma removed. The sperm pellet was resuspended to $100 \times 10^6$/ml in Kenneys modified Tyrodes medium (KMT), stained with Hoechst 33342 (5 mg/ml, Sigma-Aldrich, St. Louis Mo.), incubated for 30 min and subjected to flow cytometry. The sorted spermatozoa were centrifuged and resuspended to $40 \times 10^6$ ml in KMT in 250 µl aliquots for 48 h storage at either 4° C. or 20° C. The total progressive motility (TPM) and the acrosome status of the spermatozoa were evaluated prior to sorting and at 0, 2, 12, 24, 36 and 48 h after sorting. The TPM was evaluated microscopically and acrosomes stained with FITC-PNA (Sigma-Aldrich) and classified as intact, patchy or lost. The effect of stallions, time and storage temperatures were analyzed using the Proc GLM procedure and least means comparisons made (SAS Institute).

There was an effect of stallion (p=0.03) on sperm motility and on the proportion of intact acrosomes over time. Staining and incubating the spermatozoa with Hoechst 33342 resulted in a decrease in the proportion of intact acrosomes (Table 5). However, the proportion of intact acrosomes observed after sorting was higher than in the sperm population prior to sorting. The proportion of intact acrosomes declined (p<0.0001) as the lost acrosomes increased (p<0.0001) during 48 h after sorting, but there was no effect of time on the proportion of patchy acrosomes. There was a significant effect of sperm storage temperature after sorting such that that storage for 12 h at 20° C. resulted in higher motility than storage at 4° C. Sex-sorting spermatozoa by flow cytometry results in the selection of a population of spermatozoa which can maintain acrosome integrity for 24 h, equivalent to fresh spermatozoa. The maintenance of sperm longevity for 12 h after FACS separation should enable sex-sorted spermatozoa to be shipped to mares located some distance from the site of the flow cytometer.

TABLE 5

The motility and acrosome status of flow sorted spermatozoa over time.

| Stage of Processing | | TPM | Acrosome intact |
|---|---|---|---|
| Prestain | | 50.7 ± 10.2 | 57.1 ± 28.2 |
| Post stain | | 42.0 ± 17.1 | 42.3 ± 26.7 |
| Post incubation | | 48.0 ± 15.7 | 34.9 ± 27.1[a] |
| 0 h | Post sort | 49.9 ± 18.3 | 60.2 ± 22.3[b] |
| 2 h | 4° C. | 34.3 ± 19.3 | 47.1 ± 28.3 |
| | 20° C. | 40.8 ± 21.8 | 53.9 ± 24.5 |
| 12 h | 4° C. | 8.5 ± 12.8[a] | 59.8 ± 19.7 |
| | 20° C. | 27.0 ± 21.0[b] | 66.6 ± 12.0 |
| 24 h | 4° C. | 4.8 ± 12.9 | 56.2 ± 16.8 |
| | 20° C. | 17.2 ± 17.9 | 64.3 ± 16.4 |
| 48 h | 4° C. | 0.0 ± 0.0 | 32.7 ± 25.0 |
| | 20° C. | 5.1 ± 8.6 | 41.6 ± 24.0 |

[a,b]Values within a column with different superscripts are significantly different (p < 0.05).

Foals of predetermined sex have been accurately and reliably produced in a research setting (Lindsey et al., Equine Vet. J. 2002, 34: 128-132). Sex-sorted sperm would be more efficiently utilized by the industry, however, if frozen/thawed sex-sorted sperm were available. The objective of this study was to compare the motion characteristics of sperm that had been stored for 18 h at 15° C., flow-sorted, and then frozen, to sperm that had been cryopreserved immediately following shipment at 18 h at 15° C. Two ejaculates were used from each of five stallions. Following collection, sperm for both treatments were extended to $25 \times 10^6$/mL in a Kenney+Modified Tyrodes (KMT) medium and stored in a water bath at 15° C. for 18 h. After storage, sperm were allowed to reach ambient temperature (~22° C.) prior to centrifugation at 600 g for 10 min. Seminal plasma was removed and the sperm pellet resuspended to 500×10⁶/ml in KMT. An aliquot of sperm was removed (Control) from this sample, extended to 87×10⁶/ml in a skim-mild, egg yolk freezing extended (4% glycerol; FR5), and allowed to slow cool to 5° C. for 90 min before freezing in liquid nitrogen vapor. A second aliquot (Flow-sorted) of sperm was extended to 100×10⁶/ml in KMT, stained with Hoechst 33342 (5 mg/ml, Sigma-Aldrich, St. Louis Mo.), incubated for 30 minutes, and subsequently sorted by flow-cytometry. Sorted sperm was centrifuged at 850 g for 20 min, resuspended to 87×10⁶/ml in FR5, and allowed to cool slowly to 5° C. for 90 min prior to cryopreservation. Sperm for both treatments were packaged in 0.25-ml straws, and each straw contained 20 million sperm. Sperm were evaluated (blindly) for visual progressive motility (2 observers) at 30 and 90 min post-thaw. An aliquot of sperm from each straw was diluted in both KMT and in KMT containing 2 mM caffeine. Samples were allowed to equilibrate for 5-10 min at 37° C. prior to evaluation. A second straw of each treatment was evaluated (with and without caffeine) using the Hamilton-Thorn Motility Analyzer (CASA). Results are in Table 6. Differences in motion parameters were determined by ANOVA. According to most measured responses, flow-sorting was detrimental to sperm motility. Additionally, 2 mM caffeine improved many sperm responses. There was an interaction whereby caffeine improved some responses more for sorted sperm than for control sperm. Therefore, the damage caused by sorting can be partially compensated for by caffeine. It is possible that similar compensation may occur in the mare reproductive tract. Studies are currently in progress to compare the fertility of stored, cryopreserved stallion sperm to that of sperm that has been stored and sorted prior to cryopreservation.

TABLE 6

| Treatment | Vis 30 | Vis 90 | CASA Tot | CASA Prog | VAP | VSL | VCL | ALH | BCF | STR | LIN |
|---|---|---|---|---|---|---|---|---|---|---|---|
| C-Control | 50$^a$ | 47$^a$ | 64$^a$ | 60$^a$ | 94$^a$ | 80$^a$ | 164$^a$ | 6.19$^a$ | 33$^a$ | 83$^a$ | 50$^a$ |
| Control | 45$^a$ | 40$^b$ | 50$^b$ | 44$^b$ | 82$^a$ | 69$^a$ | 144$^a$ | 5.73$^a$ | 33$^a$ | 82$^a$ | 50$^a$ |
| C-Sorted | 32$^b$ | 31$^c$ | 32$^c$ | 21$^c$ | 48$^b$ | 38$^b$ | 98$^b$ | 4.75$^b$ | 41$^b$ | 73$^b$ | 39$^b$ |
| Sorted | 18$^c$ | 16$^d$ | 24$^d$ | 12$^d$ | 39$^b$ | 30$^b$ | 80$^b$ | 4.51$^b$ | 37$^c$ | 69$^b$ | 38$^b$ |

$^{a,b,c,d}$Values in the same column without common superscripts differ (P, 0.05).
C-treatments stimulated with 2 mM caffeine.

Cow elk 3-6-yr of age in Colorado and Minnesota were synchronized for estrus in September by insertion of a progesterone CIDR into the vagina for 12-14 d. Upon removal of the CIDR, 200 IU of eCG was administered intramuscular and elk were timed-inseminated 60 h later. Fresh semen was collected via electro-ejaculation from a 5-yr old bull elk and slowly cooled over 4 h to about 20° C. for transportation as a neat ejaculate to the sperm-sorting laboratory. The ejaculate was concentrated to 1×10⁹ sperm/ml for straining by centrifuging 1.5 ml aliquots for 10 sec at 15,000× g. Semen was incubated in 112 µM Hoechst 33342 at 200× 10⁶ sperm/ml in a TALP medium for 45 min at 34° C., and then diluted to 100×10⁶/ml for sorting. Sperm were sorted on the basis of differing DNA content of X and Y chromosome-bearing sperm. X chromosome-bearing elk sperm contained 3.8% more DNA than Y chromosome-bearing sperm. Sperm were flow-sorted over a 4 h period using MoFlo®SX operating at 50 psi with a TRIS-based sheath fluid. The 351 and 364 bands of an argon laser, emitting 150 mW, excited Hoechst 33342 dye bound to DNA. Both X and Y chromosome-bearing sperm were collected (~92% purity as verified by reanalyzing sonicated sperm aliquots for DNA) were collected at ~4,700 sperm/sec into tubes containing 2 ml of 20% egg yolk-TRIS extender. Sorted volumes of 15 ml were sequentially collected. Approximately 110×10⁶ sperm of each sex were sorted and cooled to 5° C. over 90 min. An equal volume of glycerol (12%) containing extender was added to the sorted volume at 5° C. Sorted sperm aliquots containing 30-ml were concentrated by centrifugation at 4° C. for 20 min at 850×g. Sperm pellets were pooled, adjusted to 21.7×10⁶ sperm/ml and loaded into 0.25-ml straws. Each straw, containing 5×10⁶ total sperm, was frozen in liquid nitrogen vapor. As a control, 5×10⁶ total sperm from the same ejaculate were frozen in 0.25 ml straws at the same time as the sexed sperm. After thawing for 30 sec at 37° C., 65% and 60% of sperm (control and sexed, respectively) were progressively motile as determined by visual estimates. Cows at 3 different locations and management schemes were inseminated using routine trans-cervical semen deposition in the uterine body. Pregnancy was determined 40-d post insemination by assaying blood for Pregnancy-Specific Protein B (Bio Tracking, Moscow, Idaho). Ten cows at one location were in poor condition at the time of insemination and no pregnancies were achieved with sexed or control sperm. The pregnancy rate at the other locations with sexed sperm (61%; 11/18) was similar to that for control inseminates (50%; 3/6). These pregnancy rates (sexed and controls) resulted from fewer sperm than are used in normal elk artificial insemination. Nine of eleven (82%) of sexed calves were of the predicted sex.

The invention can further include a mammal produced in accordance with any of the above described embodiments of the invention, or can include a mammal of predetermined sex in accordance with the various embodiments of the invention that provide sperm cell insemination samples having an enriched population of either X-chromosome bearing sperm cells or enriched population of Y-chromosome bearing sperm cells, or a mammal produced in accordance with any embodiment of the invention in which a sperm cell insemination sample containing a low number of sperm cells compared to the typical number used to inseminate that particular species of mammal is used, or elk progeny produced in accordance with the invention as described above.

As can be easily understood from the foregoing, the basic concepts of the present invention may be embodied in a variety of ways. It involves both a sperm cell process system including both techniques as well as devices to accomplish sperm cell processing. In this application, various sperm cell processing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this nonprovisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which will be included in a full patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "flow-sorter" should be understood to encompass disclosure of the act of "flow-sorting"—whether explicitly discussed or not—and, conversely, were there effectively disclosure of the act of "flow-sorting", such a disclosure should be understood to encompass disclosure of a "flow-sorter" and even a "means for flow-sorting" Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the sperm cell processing devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, x) the various combinations and permutations of each of the elements disclosed, and xi) each potentially dependent claim or concept as a dependency on each and every one of the independent claims or concepts presented. In this regard it should be understood that for practical reasons and so as to avoid adding potentially hundreds of claims, the applicant may eventually present claims with initial dependencies only. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

We claim:

1. A method of generating an insemination sample comprising sperm cells having at least one modified, controlled fertility characteristic, the method comprising:
   a) obtaining a sperm cell sample from a mammal, said sperm cell sample having at least one fertility characteristic;
   b) generating a fluid stream within a flow cytometer or cell sorter to provide a fluid stream pressure capable of modifying said at least one fertility characteristic in said sperm cell sample;
   c) adjusting said fluid stream pressure to control modification of said at least one fertility characteristic;
   d) exposing said sperm cell sample of a) to said fluid stream pressure of c); and
   e) collecting said sperm cell sample after said exposing step d),
   wherein said collecting of said sperm cell sample provides an insemination sample comprising sperm cells having said at least one modified, controlled fertility characteristic.

2. The method as described in claim 1, wherein said mammal is selected from the group consisting of: a bovine mammal, an equine mammal, an ovine mammal, a canine mammal, a feline mammal, a porcine mammal, a marine mammal, a cervid mammal, a primate mammal, and a caprid mammal.

3. The method as described in claim 1, further comprising the step of surrounding said fluid stream with a sheath fluid stream.

4. The method as described in claim 1, wherein said at least one fertility characteristic is selected from the group consisting of: sperm cell motility, sperm cell viability, oocyte cleavage rate, blastocyst formation rate, pregnancy rate, and a combination thereof.

5. The method as described in claim 3, wherein said sheath fluid stream includes a sheath fluid selected from the group consisting of: a phosphate buffered saline (PBS), a citrate buffer, a 2.9% sodium citrate buffer, a HEPES buffer, a TRIS-based sheath fluid, and a combination thereof.

6. The method as described in claim 3, wherein said mammal is a bovine mammal and said insemination sample comprises between about $1\times10^5$ and about $2\times10^7$ bovine sperm cells.

7. The method as described in claim 1, further comprising adjusting the fluid stream pressure of step c) incrementally to modify said at least one fertility characteristic of said sperm cell sample.

8. The method as described in claim 7, wherein adjusting said fluid stream pressure occurs between about 20 psi (0.098 kg/cm$^2$) and about 100 psi (7.03 kg/cm$^2$).

9. The method as described in claim 8, wherein said adjusting said fluid stream pressure occurs between about 30 psi (2.10 kg/cm$^2$) and about 40 psi (2.81 kg/cm$^2$).

10. The method as described in claim 9, wherein said fluid stream pressure is selected from the group consisting of: about 30 psi when sperm cell motility is the at least one fertility characteristic; about 40 psi when sperm cell motility is the at least one fertility characteristic; about 30 psi when sperm cell viability is the at least one fertility characteristic; about 40 psi when sperm cell viability is the at least one fertility characteristic; about 40 psi when oocyte cleavage rate is the at least one fertility characteristic; about 40 psi when blastocyst formation rate is the at least one fertility characteristic; and about 40 psi when pregnancy rate is the at least one fertility characteristic.

11. The method as described in claim 4, where said mammal is a bovine mammal, said at least one fertility characteristic is pregnancy rate, and pregnancy rate is determined as the number of pregnancies resulting from insemination of a female bovine mammal with said insemination sample comprising sperm cells having at least one modified, controlled fertility characteristic.

12. The method as described in claim 2, wherein the mammal is a bovine mammal and said insemination sample contains between $1\times10^6$ and $3\times10^6$ bovine sperm cells.

13. The method as described in claim 1, further comprising sorting the sperm cells in said insemination sample by X-chromosome or Y-chromosome.

* * * * *